(12) United States Patent
Pillai et al.

(10) Patent No.: US 10,828,293 B2
(45) Date of Patent: *Nov. 10, 2020

(54) ANTI-INFECTIVE METHODS, COMPOSITIONS, AND DEVICES

(71) Applicant: DOW PHARMACEUTICAL SCIENCES, INC., Petaluma, CA (US)

(72) Inventors: Radhakrishnan Pillai, Santa Rosa, CA (US); Gordon Dow, Greenbrae, CA (US)

(73) Assignee: DOW PHARMACEUTICAL SCIENCES, INC., Petaluma, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/353,849

(22) Filed: Mar. 14, 2019

(65) Prior Publication Data

US 2019/0209543 A1 Jul. 11, 2019

Related U.S. Application Data

(63) Continuation of application No. 14/552,307, filed on Nov. 24, 2014, now Pat. No. 10,245,257.

(60) Provisional application No. 61/907,401, filed on Nov. 22, 2013.

(51) Int. Cl.
| | |
|---|---|
| *A61K 31/454* | (2006.01) |
| *A61K 47/24* | (2006.01) |
| *A61K 47/14* | (2017.01) |
| *A61K 47/10* | (2017.01) |
| *A61K 47/12* | (2006.01) |
| *A61K 9/00* | (2006.01) |
| *A61K 47/06* | (2006.01) |
| *A61K 47/18* | (2017.01) |

(52) U.S. Cl.
CPC .......... *A61K 31/454* (2013.01); *A61K 9/0014* (2013.01); *A61K 47/06* (2013.01); *A61K 47/10* (2013.01); *A61K 47/12* (2013.01); *A61K 47/14* (2013.01); *A61K 47/18* (2013.01); *A61K 47/24* (2013.01); *Y10T 83/0443* (2015.04)

(58) Field of Classification Search
CPC .... A61K 31/454; A61K 9/0014; A61K 47/06; A61K 47/12; A61K 47/14; A61K 47/183; A61K 47/24

See application file for complete search history.

(56) References Cited

U.S. PATENT DOCUMENTS

| | | |
|---|---|---|
| 3,655,290 A | 4/1972 | Griffith |
| 4,052,513 A | 10/1977 | Kaplan |
| 4,384,589 A | 5/1983 | Morris |
| 4,457,938 A | 7/1984 | von Bittera |
| 4,912,124 A | 3/1990 | Das |
| 4,985,455 A | 1/1991 | Motono et al. |
| 5,208,257 A | 5/1993 | Kabara |
| 5,391,367 A | 2/1995 | DeVincentis et al. |
| 5,449,715 A | 9/1995 | Plochocka et al. |
| 5,461,068 A | 10/1995 | Thaler |
| 5,549,930 A | 8/1996 | Reysis |
| 5,578,641 A | 11/1996 | Jackson et al. |
| 5,588,447 A | 12/1996 | Gueret |
| 5,620,994 A | 4/1997 | Naito et al. |
| 5,696,105 A | 12/1997 | Hackler |
| 5,696,164 A | 12/1997 | Sun |
| 5,716,969 A | 2/1998 | Naito et al. |
| 5,750,137 A | 5/1998 | Taskovich et al. |
| 5,814,305 A | 9/1998 | Laugier |
| 5,874,069 A | 2/1999 | Mendolia |
| 5,916,545 A | 6/1999 | Burnett et al. |
| 5,962,476 A | 10/1999 | Naito et al. |
| 5,997,893 A | 12/1999 | Jampani et al. |
| 6,022,551 A | 2/2000 | Jampani et al. |
| 6,040,266 A | 3/2000 | Fay et al. |
| 6,042,845 A | 3/2000 | Sun et al. |
| 6,080,393 A | 6/2000 | Liu et al. |
| 6,080,416 A | 6/2000 | Jampani et al. |
| 6,165,484 A | 12/2000 | Raad et al. |

(Continued)

FOREIGN PATENT DOCUMENTS

| | | |
|---|---|---|
| CA | 2673976 A1 | 7/2008 |
| CA | 2706114 A1 | 7/2009 |

(Continued)

OTHER PUBLICATIONS

Abrutyn (1999) "Chapter 8: Organo-Modified Siloxane Polymers for Conditioning Skin and Hair Conditioning Agents for Hair and Skin" (Randy Schueller & Perry Romanowski, eds.).

Abstract No. F78. The Abstracts of the Interscience Conference on Antimicrobial Agents and Chemotherapy (ICAAC), 36th ICAAC, held on Sep. 15-18, New Orleans, LA, 1996.

Abstract No. F79. The Abstracts of the Interscience Conference on Antimicrobial Agents and Chemotherapy (ICAAC), 36th ICAAC, held on Sep. 15-18, New Orleans, LA, 1996.

Abstract No. F80. The Abstracts of the Interscience Conference on Antimicrobial Agents and Chemotherapy (ICAAC), 36th ICAAC, held on Sep. 15-18, New Orleans, LA, 1996.

(Continued)

*Primary Examiner* — James D. Anderson
(74) *Attorney, Agent, or Firm* — Kilpatrick Townsend & Stockton LLP

(57) ABSTRACT

The present invention provides methods for treating onychomycosis. In certain embodiments, the methods comprise comprising applying a pharmaceutically acceptable formulation containing 10% efinaconazole once a day for a treatment period of at least 36 weeks to the treatment area of an onychomycosis patient (a) without debriding the nail or nail-associated tissue initially or during the treatment period and/or (b) without removing the formulation from the treatment area during the treatment period. In certain embodiments, the formulation also comprises water, cyclomethicone, diisopropyl adipate, alcohol, C12-15 alkyl lactate, butylated hydroxytoluene, citric acid anhydrous, and disodium edetate.

18 Claims, 6 Drawing Sheets

(56) References Cited

U.S. PATENT DOCUMENTS

| | | |
|---|---|---|
| 6,176,631 B1 | 1/2001 | Gueret |
| 6,197,305 B1 | 3/2001 | Friedman |
| 6,207,142 B1 | 3/2001 | Odds et al. |
| 6,231,875 B1 | 5/2001 | Sun |
| 6,264,927 B1 | 7/2001 | Monahan |
| 6,306,375 B1 | 10/2001 | Ellingson et al. |
| 6,433,073 B1 | 8/2002 | Kantner et al. |
| 6,538,039 B2 | 3/2003 | Laurent |
| 6,585,963 B1 | 7/2003 | Quan |
| 6,676,953 B2 | 1/2004 | Hexamer |
| 6,740,326 B1 | 5/2004 | Meyer |
| 6,821,508 B2 | 11/2004 | Zatz |
| 6,846,837 B2 | 1/2005 | Maibach |
| 7,026,308 B1 | 4/2006 | Gavin et al. |
| 7,094,422 B2 | 8/2006 | Chew et al. |
| 7,214,506 B2 | 5/2007 | Tatsumi |
| 7,582,621 B2 | 9/2009 | Baker et al. |
| 7,622,844 B1 | 11/2009 | Kuhlmann-Wilsdorf |
| 7,950,865 B2 | 5/2011 | Albisetti |
| 8,039,494 B1 | 10/2011 | Winckle et al. |
| 8,486,978 B2 | 7/2013 | Winckle et al. |
| 9,302,009 B2 | 4/2016 | Winckle et al. |
| 9,566,272 B2 | 2/2017 | Winckle et al. |
| 9,662,394 B2 | 5/2017 | Bhatt |
| 9,861,698 B2 | 1/2018 | Winckle et al. |
| 9,877,955 B2 | 1/2018 | Winckle et al. |
| 10,105,444 B2 | 10/2018 | Winckle et al. |
| 10,245,257 B2 * | 4/2019 | Pillai ................. A61K 47/18 |
| 10,342,875 B2 * | 7/2019 | Bhatt ................. A61K 31/454 |
| 10,478,601 B2 | 11/2019 | Ueta et al. |
| 10,512,640 B2 | 12/2019 | Winckle et al. |
| 2002/0022660 A1 | 2/2002 | Jampani et al. |
| 2002/0183387 A1 | 12/2002 | Bogart |
| 2003/0007939 A1 | 1/2003 | Murad |
| 2003/0075201 A1 | 4/2003 | Saito |
| 2003/0082129 A1 | 5/2003 | Buckingham |
| 2004/0180025 A1 | 9/2004 | Long |
| 2005/0129641 A1 | 6/2005 | Arnaud et al. |
| 2005/0142094 A1 | 6/2005 | Kumar |
| 2005/0176650 A1 | 8/2005 | Heasley |
| 2005/0181999 A1 | 8/2005 | Ferrandis et al. |
| 2005/0186161 A1 | 8/2005 | Kawase |
| 2005/0244342 A1 | 11/2005 | Friedman |
| 2005/0281750 A1 | 12/2005 | Willcox et al. |
| 2006/0008538 A1 | 1/2006 | Wu et al. |
| 2006/0110415 A1 | 5/2006 | Gupta |
| 2006/0147383 A1 | 7/2006 | Mallard |
| 2006/0165747 A1 | 7/2006 | Rolf |
| 2006/0234981 A1 | 10/2006 | Baker et al. |
| 2006/0280706 A1 | 12/2006 | Sebillotte-Arnaud |
| 2007/0041910 A1 | 2/2007 | Pitre |
| 2007/0071705 A1 | 3/2007 | De Oliveira |
| 2007/0082039 A1 | 4/2007 | Jones et al. |
| 2007/0082375 A1 | 4/2007 | Tatsumi et al. |
| 2007/0142317 A1 | 6/2007 | Warren et al. |
| 2007/0142478 A1 | 6/2007 | Xia et al. |
| 2007/0155699 A1 | 7/2007 | Baker et al. |
| 2007/0207107 A1 | 9/2007 | Winckle et al. |
| 2007/0207222 A1 | 9/2007 | Yu et al. |
| 2007/0243218 A1 | 10/2007 | Ellinghuysen et al. |
| 2008/0233179 A1 | 9/2008 | Grenier et al. |
| 2008/0317684 A1 | 12/2008 | Spann-Wade et al. |
| 2009/0030059 A1 | 1/2009 | Miki et al. |
| 2009/0175810 A1 | 7/2009 | Winckle |
| 2010/0298394 A1 | 11/2010 | Steiner et al. |
| 2010/0317695 A1 | 12/2010 | Okumura et al. |
| 2012/0010246 A1 | 1/2012 | Winckle et al. |
| 2012/0071533 A1 | 3/2012 | Vontz et al. |
| 2013/0064872 A1 | 3/2013 | Jung et al. |
| 2013/0150586 A1 | 6/2013 | Mimura et al. |
| 2014/0228403 A1 | 8/2014 | Winckle et al. |
| 2019/0076531 A1 | 3/2019 | Winckle et al. |
| 2019/0358329 A1 | 11/2019 | Bhatt et al. |

FOREIGN PATENT DOCUMENTS

| | | |
|---|---|---|
| CA | 2391274 C | 12/2010 |
| CN | 1076614 A | 9/1993 |
| DE | 41306 | 9/1965 |
| EP | 0211555 A2 | 2/1987 |
| EP | 1205559 A1 | 5/2002 |
| EP | 1273299 A1 | 1/2003 |
| GB | 2407496 | 10/2003 |
| JP | H10226639 A | 8/1998 |
| JP | H11-214369 A | 8/1999 |
| JP | 3608209 B2 | 1/2005 |
| JP | 2009-263346 A | 11/2009 |
| JP | 2011-508774 A1 | 3/2011 |
| WO | 87/02580 | 5/1987 |
| WO | 93/15719 A1 | 8/1993 |
| WO | 1994/026734 A1 | 11/1994 |
| WO | 95/03775 A1 | 2/1995 |
| WO | 96/19186 A1 | 6/1996 |
| WO | 96/30011 A1 | 10/1996 |
| WO | 98/43673 A1 | 10/1998 |
| WO | 99/49835 | 10/1999 |
| WO | 1999/051192 A2 | 10/1999 |
| WO | 01/07643 | 2/2001 |
| WO | 01/08529 A2 | 2/2001 |
| WO | 2004/021968 A2 | 3/2004 |
| WO | 2004/084826 | 10/2004 |
| WO | 2005/053666 A1 | 6/2005 |
| WO | 2007/070643 A2 | 6/2007 |
| WO | 2007/102241 A1 | 9/2007 |
| WO | 2007/103555 A2 | 9/2007 |
| WO | 2008/017914 A | 2/2008 |
| WO | 2009/085314 A1 | 7/2009 |
| WO | 2010/090654 A1 | 8/2010 |
| WO | 2010/100252 A1 | 9/2010 |
| WO | 2011/008770 A2 | 1/2011 |
| WO | 2011/064558 A2 | 6/2011 |
| WO | 2011/073395 A1 | 6/2011 |
| WO | 2011/145765 A1 | 11/2011 |
| WO | 2012/005973 A1 | 1/2012 |
| WO | 2013/130666 A1 | 9/2013 |

OTHER PUBLICATIONS

Adams, A. et al. (Jun. 2009) "LC Stability Studies of Voriconazole and Structural Elucidation of Its Major Degradation Product." *Chroma* 69(Suppl 2): 115.

Ahmed et al. (1983) "The Behaviour of Phenolic Antioxidants, Synergists and their Mixtures in Two Vegetable Oils" *European Journal of Lipid Science and Technology* 85(12): 479-483.

Benvenuti. "Ingredient Spotlight: Disodium EDTA," *FutureDerm* (Sep. 30, 2013).

Colas, A. et al. (Oct. 2005) "Silicones in new pharmaceutical developments, from formulations to manufacturing processes." *PharmaChem*, 2005, 46-49.

Connors, K.A. et al. (1986) "Chapter 5, Oxidation and Photolysis,"*Chemical Stability of Pharmaceuticals*, Second Ed., John Wiley & Sons, New York, USA, pp. 82-114.

Del Rosso, J. et al., "Efinaconazole 10% solution a new topical treatment for onychomycosis: contact sensitization and skin irritation potential," Journal of Clinical and Aesthetic Dermatology, 6(3):20-24, 2013.

Douglas. (Dec. 11, 2002) Reuters News Service, "New topical triazole superior to other agents in nail fungal model".

Elewski, B. et al., "Efinaconazole 10% solution in the treatment of toenail onychomycosis: Two phase III multicenter, randomized, double-blind studies," J. Am. Acad. Dermatol., 68(4):600-608, 2013.

Elewski, B. et al., "Onchomycosis: an overview," J. Drugs Dermatol., 12(7 Suppl. 2):s96-s103, 2013.

Elewski, B., "Efinaconazole 10% solution: a new topical antifungal therapy for onychomycosis," Expert Rev. Dermatol., 8(4):347-356, 2013.

Ghanem, et al. (1987) "The Effects of Ethanol on the Transport of 13-Estradiol and Other Permeants in Hairless Mouse Skin" Journal of Controlled Release, 6, 75-83.

(56) References Cited

OTHER PUBLICATIONS

Hay R.J. et al. (Mar. 1985) "Tioconazole Nail Solution—an Open Study of its Efficacy in Onychomycosis." *Clinical and Experimental Dermatology*, 10, 111-115.
Inagi et al. (1981) "Influence of Vehicle Composition on the Penetration of Indomethacin through Guinea-Pig Skin" Chem. Pharm. Bull. 29(6), 1708-1714.
International Search Report, PCT/US2014/067184, dated Sep. 17, 2015, 1 page.
Jannsen Pharmaceuticals, "Pevaryl®" (Mar. 2009), 3 pages.
Jarratt, M. et al., "Safety and pharmacokinetics of Efinaconazole 10% solution in healthy volunteers and patients with severe onychomycosis," J. Drugs Dermatol., 12(9):1010-1016, 2013.
Jo Siu, W. et al., "Comparison of in vitro antifungal activities of Efinaconazole and currently available antifungal agents against a variety of pathogenic fungi associated with onychomycosis," Antimicrobial Agents and Chemotherapy, 57(4):1610-1616, 2013.
Li et al. (2009) "Antioxidant System for the Preservation of Vitamin A in Ultra Rice," *Food and Nutrition Bulletin* 30(1): 82-89.
Lofty, H. et al. (2012) "Novel Spectrophotometric Methods for the Determination of Fluconazole in the Presence of Its Oxidative Degradation Product." *J. Chil. Chem. Soc.*, 57(4), 1447-1455.
Murdan (Apr. 2002) "Drug delivery to the nail following topical application." *Int. J. of Pharmaceutics.* 236(1-2): 1-26.
Norwich Pharmacal Co. (Jun. 29, 1953) "Triple-Action + Penetration Beats Athlete's Foot." *Life Magazine*, p. 96.
Notabartolo, J., "Dermatology market watch onychomycosis rediscovering topical antifungal therapy," J. Dermatol. Phys. Assist., 7(3):13-14, 2013.
Ogura, et al. "Synthesis and Antifungal Activities of (2R,2R)-2-Aryl-1-azolyl-3-(substituted amino)-2-butanol Derivatives as Topical Antifungal Agents," *Chem. Pharm. Bull.* 47(10) 1417-1425 (1999).
Penlac™ Nail Lacquer Prescription Label (Dec. 1999, pp. 1-13, accessed from http://www.accessdata.fda.gov/drugsatfda_docs/label/1999/210221bl.pdf on Dec. 14, 2015).
Pollak, R. Jan. 22, 2013 "Could Efinaconazole 10% have an impact for onychomycosis? Online Case Study" *Podiatry Today* vol. 26, Issue 2, 7 pages.
Reinel, et al. (1992) "Topical Treatment of Onychomycosis with Amorolfine 5% Nail Lacquer: Comparative Efficacy and Tolerability of Once and ☐ Twice Weekly Use," *Dermatol.* 184, 21-24.
Relyveld, G et al., "Benzoyl peroxide/clindamycin/UVA is more effective than fluticasone/UVA in progressive macular hypomelanosis: a randomized study," J. Am. Acad. Dermatol., 55:836-43, 2006.
Remington, (2006) "Chapter 39: Solutions, Emulsions, Suspension, and Extracts." *The Science and Practice of Pharmacy, 21st Ed.*, pp. 747-749.
Rich, P., "Topical treatment of onychomycosis with efinaconazole solution 10%," Cutis, 91:305-307, 2013.
Rowe, et al., (2006) "Citric Acid." *Handbook of Pharmaceutical Excipients*, Fifth ed., The American Pharmacists Association. p. 185-187.
Rowe, et al., (2006) "Edetic acid." *Handbook of Pharmaceutical Excipients*, Fifth ed., The American Pharmacists Association. pp. 260-263.
Rowe, et al., (2009) "Butylated Hydroxytoluene." *Handbook of Pharmaceutical Excipients*, Sixth ed., Pharmaceutical Press. pp. 75-76.
Rowe, et al., (2009) "Citric Acid Monohydrate" *Handbook of Pharmaceutical Excipients*, Sixth ed., Pharmaceutical Press. pp. 181-183.
Rowe, et al., (2009) "Edetic Acid." *Handbook of Pharmaceutical Excipients*, Sixth ed., Pharmaceutical Press. pp. 247-250.
Rowe, et al., (2009) "Polyethylene Glycol." *Handbook of Pharmaceutical Excipients*, Sixth ed., Pharmaceutical Press. pp. 517-521.
Scientific Committee on Consumer Products (SSCP) Opinion on Octamethylcyclotetrasiloxane (D4), Cyclomethicone (INCI name) dated Dec. 13, 2005.
Siddiqui et al. (2010) "Analytical Reflectance Spectroscopic Method for Analysis of Iron Oxide Lake Dye Coating Solutions," *Karachi University Journal of Science*, 38, pp. 1-5.
Smith, E. et al. (2002) "Topical Dermatological Vehicles: A Holistic Approach." *Topical Absorption of Dermatological Products*; Bronaugh, R. L., Maibach, H. I., Eds; Marcel Dekker, Inc.: New York, United States; pp. 457-463.
Tatsumi et al., Therapeutic efficacy of topically applied KP-103 against experimental Tinea Unguium in Guinea Pigs in comparison with Amorolfine and Terbinafine, Antimicrobial Agents and Chemotherapy, vol. 46, No. 12, pp. 3797-3801 (Dec. 2002).
Tatsumi Y., et al (2002) "In Vivo Fungicidal Effect of KP-103 in a Guinea Pig Model of Interdigital Tinea Pedis Determined by Using a New Method for Removing the Antimycotic Carryover Effect", *Microbiol. Immunol.* 46(7): 433-439.
Tatsumi Y., et al. (2002) "KP-103, a novel triazole derivative, is effective in preventing relapse and successfully treating experimental interdigital Tinea Pedis and Tinea Corporis in guinea pigs," *Microbiol. Immunol.* 46(7): 425-432.
Tatsumi Y., et al. (May 2001) "In Vitro Antifungal Activity of KP-103, A Novel Triazole Derivative, and its Therapeutic Efficacy Against Experimental Plantar Tinea Pedis and Cutaneous Candidiasis in Guinea Pigs," *Antimicrobial Agents and Chemotherapy*, 45(5): 1493-1499.
Tatsumi, Y. et al., "Mechanism of action of Efinaconazole, a novel triazole antifungal agent," Antimicrob. Agents Chemother., 57(5):2405-2409, 2013.
Tosti, A., "Efinaconazole solution 10%: Topical antifungal therapy for toenail onychomycosis," Cutis., 92:203-208, 2013.
Tschen et al., "Efinaconazole Solution in the Treatment of Toenail Onychomycosis: A Phase 2, Multicenter, Randomized, Double-Blind Study," JDD, vol. 12, No. 2, pp. 186 192, Feb. 2013 [retrieved Jan. 20, 2015]. Retrieved from the Internet, http://jddonline.com/articles/dermatology/S1545961613P0186X.
Tsukioka. (May 11, 2006) *Japan Corporate News*, "Kaken Pharmaceutical to license its antifungal compound KP-103 to Dow Pharmaceutical Sciences".
USP 23 NF 18 (1995) Chapter <1061> "Color—Instrumental Measurement" *The United States Pharmacopeia—The National Formulary*. pp. 1860-1861.
USP 23 NF 18 (1995) Chapter <851> "Spectrophotometry and Light-Scattering" *The United States Pharmacopeia—The National Formulary*. pp. 1830-1835.
Valeant Pharmaceuticals International Inc., "Valeant Pharmaceuticals Announces Approval of Jublia® For the Treatment of Onychomycosis in Canada," News Release 1-2, Oct. 3, 2013 [retrieved Jan. 20, 2015]. Retrieved from the Internet, http://ir.valeant.com/investor-relations/news-releases/news-release-details/2013/Valeant-Pharmaceuticals-Announces-Approval-Of-Jublia-For-The-Treatment-Of-Onychomycosis-In-Canada/default.aspx.
Valeant Pharmaceuticals North America LLC, "JUBLIA® (efinaconazole) topical solution, 10%," Patient Information and Instructions for Use, Revised Jun. 2014, retrieved online at URL: https://www.accessdata.fda.gov/drugsatfda_docs/label/2014/203567s000lbl.pdf on Apr. 11, 2017, 13 pages.
Vanderdonckt et al., "Miconazole alcoholic solution in the treatment of mycotic nail infections," Mykosen, 19(17):251-256 (Sep. 1975).
Walters, K.A. et al. (1983) "Permeability characteristics of human nail plate." *International Journal of Cosmetic Science*, 5, 231-246.
Japan Pharmaceutical Excipients Council, "Disodium Edetate," and "Anhydrous Citric Acid," Japanese Pharmaceutical Excipient Directory, Jul. 25, 2007, ISBN 9784840809863, pp. 39-291.
Valeant Canada LP, "$^{Pr}$Jublia™ Efinaconazole Topical Solution, 10% w/w, Topical Antifungal Agent," Product Monograph, Oct. 2, 2013, 24 pages.
Aly, R., "Ecology and epidemiology of dermatophyte infections" (Paper delivered at the International Summit on Cutaneous Antifungal Therapy) J. Am. Acad. Dermatol. 31, S21-S25 (1994).
Arika, T., et al., "Nishinihon Hifuka" Nishinihon J. Dermatol. 52, 545-549 (1990) [Certified English Translation].
Baden, H.P., et al., "A comparative study of the physiochemical properties of human keratinized tissues" Biochim. Biophys. Acta 322, 269-278 (1973).

(56) References Cited

OTHER PUBLICATIONS

Bhatt, Varsha. Development of an optimal formulation for efinaconazole a novel antifungal agent for the treatment of onychomycosis by topical application, J. Am. Acad. Dermatol. 68(4):AB104, Apr. 2, 2013.
Buck, D.S., et al., "Comparison of two topical preparations for the treatment of Onychomycosis: Melaleuca alternifolia (Tea Tree) oil and clotrimazole" J. Fam. Pract. 38(6), 601-605 (1994).
Burch, G.E. & Winsor, T., "Diffusion of water through dead plantar, palmar and tarsal human skin and through toe nails" Arch Derm. Syphilol. 53, 39-41 (1946).
Ceschin-Rogues, C G., et al., "Ciclopirox nail lacquer 8%: In vivo penetration into and through nails and in vitro effect on pig skin" Skin Pharmacol. 4, 89-94 (1991).
Elewski, B.E. & Hay R.J., "Update on the management of onychomycosis: Highlights of the Third annual international summit on cutaneous antifungal therapy" In: Clinical Infectious Diseases vol. 23 No. 2 Aug. 1996 (Chicago, IL: The University of Chicago Press, 1996) pp. 305-313.
Elewski, B.E., "Onychomycosis" Fitzpatrick's J. Clin. Dermatol. Nov./Dec., 48-54 (1994).
Elewski, B.E., "Onychomycosis: Pathogenesis, diagnosis, and management" C/in. Microbiol. Rev. 11(3), 415-429 (1998).
Elewski, B.E., "Trends in the management of cutaneous fungal infections" Jpn. J. Med. Mycol. 36, 7-12 (1995).
Franz, T.J., "Absorption of amorolfine through human nail" Dermato/, 184(Supp I 1 ) , 18-20 (1992).
Goodman and Gilman's The Pharmacological Basis of Therapeutics. 10th Edition, edited by Hardman, Limbird, and Gilman. McGraw Hill, New York (2001) Chapter I, pp. 3-29.
Haria, M. & Bryson, H.M. , "Amorolfine: A review of its pharmacological properties and therapeutic potential in the treatment of onychomycosis and other superficial fungal infections" Drugs, 49(1), 103-120 (1995).
Hay, R.J., "Leading articles: The azole antifungal drugs" J. Antimicrob. Chemother. 20, 1-5 (1987).
Japan Pharmaceutical Excipients Council, Revised Pharmaceutical Additives Handbook, Yakuji Nippo Limited, Feb. 28, 2007, pp. 407-408.
Kobayashi, Y., et al., "Enhancing effect of N-acetyl-L-cysteine or 2-mercaptoethanol on the in vitro permeation of 5-fluorouracil or tolnaftate through the human nail plate" Chem. Pharm. Bull. 46(11), 1797-1802 (1998).
Marty, J-P. L., "Amorolfine nail lacquer: A novel formulation" J. Eur. Acad. Dermatol. Venereal. 4(Suppl. 1), S17-S21 (1995).
Mertin, D. & Lippold, B.C., "In-vitro permeability of the human nail and of a keratin membrane from bovine hooves: Influence of the partition coefficient octanol/water and the water solubility of drugs on their permeability and maximum flux" J. Pharm. Pharmacol. 49(1), 30-34 (1997).
Mertin, D. & Lippold, B.C., "In-vitro permeability of the human nail and of a keratin membrane from bovine hooves: Penetration of chloramphenicol from lipophilic vehicles and a nail lacquer" J. Pharm. Pharmacol. 49(3), 241-245 (1997).
Mertin, D. & Lippold, B.C., "In-vitro permeability of the human nail and of a keratin membrane from bovine hooves: Prediction of the penetration rate of antimycotics through the nail plate and their efficacy" J. Pharm. Pharmacol. 49(9), 866-872 (1997).
Niewerth, M. & Korting, H.C., "Management of onychomycoses" Drugs 58(2), 283-296 (1999).
Odom, R.B. "New therapies for onychomycosis" (Paper delivered at the symposium "Onychomycosis: Issues and observations") J. Am. Acad. Dermatol. 35, S26-S30 (1996).
Quintanar-Guerrero, D. et al., "The effect of keratolytic agents on the permeability of three imidazole antimycotic drugs through the human nail" Drug Dev. Ind. Pharm. 24(7), 685-690 (1998).
Roberts, D.T., et al., "Guidelines for treatment of onychomycosis" Brit. J. Dermatol. 148, 402-410 (2003).
Scher, R.K., "Onychomycosis: therapeutic update" J. Am. Acad. Dermatol. 40, S21-S26 (1999).
Spruit, D., "Measurement of water vapor loss through human nail in vivo" J. Investig. Dermatol. 56(5), 359-391 (1971).
Stuttgen, G. & Bauer, E., "Bioavailability, skin and nail penetration of topically applied antimycotics" Mykosen, 25(2), 74-80 (1992).
Summerbell, R.C., "Epidemiology and ecology of onychomycosis" Dermatol. 194(Supp. 1), 32-36 (1997).
USP 23 NF 18 (1995) Chapter 631 "Color and Achromicity" *The United States Pharmacopeia—The National Formulary*. pp. 1779-1780.
Van Hoogdalem, E.J., "Nail penetration of the antifungal agent oxiconazole after repeated topical application in health volunteers, and the effect of acetylcysteine" Eur. J. Pharm. Sci. 5, 119-127 (1997).
Walters, K.A. et al., "Penetration of the human nail plate: The effects of vehicle pH on the permeation of micronazole" J. Pharm. Pharmacol. 37, 771-775 (1985).
Walters, K.A. et al., "Physiochemical characterization of the human nail: Solvent effects on the permeation of homologous alcohols" J. Pharm. Pharmacol. 37, 498-499 (1985).
Walters, K.A. et al., "Physiochemical characterization of the human nail: Permeation pattern for water and the homologous alcohols and differences with respect to the stratum corneum" J. Pharm. Pharmacol. 35, 28-33 (1983).
Walters, K.A. et al., "Physiochemical characterization of the human nail: I. Pressure sealed apparatus for measuring nail plate permeabilities" J. Invest. Dermatol. 76, 76-79 (1981).
Wang, Shihua et al. "Effect of Disodium EDTA on the Stability and Efficacy of Compound Ketoconazole Cream" *West China Journal of Pharmaceutical Sciences*, vol. 22, No. 2, pp. 236-237 (Dec. 31, 2007).
Hartman, P.G. and D. Sanglard, "Inhibitors of Ergosterol Biosynthesis as Antifungal Agents," Current Pharmaceutical Design, 1997, vol. 3, No. 2, 177-208.
Sun et al., "Nail Penetration." Chap. 30 in *Topical Absorption of Dermatological Products*. New York: Marcel Dekker, Inc., 2001.
Nicotra, F., "4.2.2. Antioxidants," in Organic and Bio-molecular Chemistry, vol. 2, Encyclopedia of Life Support Systems, pp. 68-71, 2009.
Raghavan, R. and Joseph, J., "Spectroscopic Methods of Analysis: Ultraviolet and Visible Spectrophotometry," Encyclopedia of Pharmaceutical Technology, 3rd Ed. vol. 1, pp. 3460-3475, 2007.

\* cited by examiner

ANTI-INFECTIVE METHODS, COMPOSITIONS, AND DEVICES

CROSS REFERENCES TO RELATED APPLICATIONS

The present application is a continuation of U.S. patent application Ser. No. 14/552,307, filed Nov. 24, 2014, which claims priority to U.S. Provisional Patent Application No. 61/907,401, filed on Nov. 22, 2013, which application is incorporated herein by reference in its entirety for all purposes.

FIELD OF THE INVENTION

The inventions described herein relate to methods, compositions, and devices for treating onychomycosis and/or inhibiting and/or eradicating microorganisms.

BACKGROUND OF THE INVENTION

Onychomycosis is a common, chronic, and recurring fungal infection of the toenails or, less frequently, the fingernails. Onychomycosis is the most common nail disorder in adults, accounting for about half of all nail disorders, with an estimated prevalence in the United States of nearly 14%. While not life threatening, the disease should not be considered purely a cosmetic problem. Significant physical and psychological effects, such as pain and decreased self-esteem, may occur.

Current onychomycosis treatment strategies include both oral and topical antifungal agents (such as itraconazole (Sporanox®) and terbinafine (Lamisil®)), but the successful management of the disease can be challenging. An oral antifungal currently is the preferred first line therapy because of its superior efficacy and shorter treatment duration. Ciclopirox lacquer (approved by the U.S. Food and Drug Administration in 1999 as Penlac® Nail Lacquer and now available in various generics), has demonstrated modest efficacy in treating mild to moderate onychomycosis not involving the lunula (Gupta 2005) with reported complete cure rates of 5.5% to 8.5% (Gupta 2000b). Frequent debridement is required when using this product.

SUMMARY OF THE INVENTION

The invention provides new methods of treating onychomycosis and/or killing or inhibiting microorganisms through administration of efinaconazole formulations. The methods lack many of the steps that prior onychomycosis therapies required in order to be effective and include steps for improved administration of efinaconazole formulations resulting in surprising efficacy rates.

In one aspect, the invention provides a method of treating onychomycosis comprising applying a pharmaceutically acceptable formulation comprising about 10% w/w efinaconazole (e.g., 8-12% efinaconazole, 9-11% w/w efinaconazole, or approximately 10% w/w efinaconazole) once a day for a treatment period of at least 36 weeks to the treatment area of an onychomycosis patient (a) without debriding the nail or nail-associated tissue initially or during the treatment period and/or (b) without removing the formulation from the treatment area during the treatment period. In a preferred aspect, the method is performed both (a) without debriding the nail or nail-associated tissue initially or during the treatment period, and (b) without removing the formulation from the treatment area during the treatment period. In another preferred aspect, the method is performed both (a) without debriding the nail or nail-associated tissue initially or during the treatment period, and (b) without removing the formulation from the treatment area during the treatment period, and further (c) without occluding the treatment area. The efinaconazole can be the only active pharmaceutical ingredient (API) or the only anti-onychomycosis API used in the method in one aspect. The method is performed for 48 weeks also or alternatively in several aspects.

In another aspect, the method also or alternatively includes the step of requiring that the patient wait at least 10 minutes before administering the formulation if the treatment area was previously in contact with water. In another aspect, the method can require a step of cleaning the treatment area prior to administering the efinaconazole formulation. If a cleaning step is required, the method can require the patient to wait for at least 10 minutes before administering the formulation if the cleaning includes wetting the treatment area with water.

In one aspect, methods are performed with an efinaconazole formulation comprising a vehicle that is volatile and/or that rapidly penetrates the nail and a wetting agent. In one embodiment, the vehicle is an alcohol and the wetting agent is a volatile silicone. In other embodiments, the formulation also or alternatively comprises an amount of butylated hydroxytoluene (BHT), and an amount of a salt of ethylenediaminetetraacetic acid (EDTA), the amounts of BHT and EDTA being sufficient to ensure the composition is (i) colorless upon initial manufacturing of the composition and (ii) colorless or pale yellow after storage for at least three weeks at a temperature of at least about 40° C.

The method can include the requirement that the efinaconazole formulation is not administered in an occlusive or semi-occlusive manner. The method also or alternatively can include the step of having the user uniformly spread the efinaconazole formulation throughout the treatment area with an applicator. In certain embodiments, the method includes administering the efinaconazole formulation from a suitable container that is in fluid communication with an applicator, loading the applicator, and applying the efinaconazole with the applicator. The efinaconazole can be applied in a dropwise fashion, or by spreading a portion of the formulation in a continuous fashion.

In another exemplary aspect, the invention provides a method for treating onychomycosis which method includes (a) providing a container that is suitable for storing an efinaconazole formulation for pharmaceutical use, the container comprising an applicator that is capable of dispensing a pharmaceutically effective dose of an efinaconazole solution and spreading an approximately uniform amount of the efinaconazole formulation to or on a target area by manual action after loading, (b) loading the applicator with the dose of the efinaconazole formulation, and (c) administering the dose of the efinaconazole formulation to the treatment area of each treated toe by uniform manual spreading. In a particular exemplary embodiment, the container is a squeeze sensitive container and the applicator is a flow through applicator which delivers efinaconazole formulation to the target area when a user applies sufficient pressure on the container.

In another exemplary aspect, the invention provides a method for treating onychomycosis comprising applying a pharmaceutically acceptable 8-15% efinaconazole formulation to a treatment area of an onychomycosis patient once a day for at least 36 weeks in a manner such that the concentration of efinaconazole in the nail is between 5000 µg and 9000 µg per gram of sample toenail tissue analyzed.

Still another aspect of the invention is a device for treating fungal infections comprising (a) a container portion that securely holds a flowable pharmaceutical formulation of efinaconazole and that can maintain the formulation in a pharmaceutically acceptable state for extended periods of time at room temperature, (b) a loading portion that is capable of being loaded with a desired dose of the efinaconazole formulation when a user desires to apply a treatment, and (c) means for delivering the dose of the efinaconazole formulation by manual application evenly across the treatment area of a toe.

In another aspect of the invention, a method of treating onychomycosis is provided, the method comprising applying a pharmaceutically acceptable efinaconazole formulation once a day for a treatment period of at least 36 weeks to the treatment area of an onychomycosis patient (a) without debriding the nail or nail-associated tissue in the treatment area initially or during the treatment period, (b) without removing the formulation from the treatment area during the treatment period, and (c) without occluding the treatment area; wherein the efinaconazole formulation comprises 8-12% w/w efinaconazole, water, cyclomethicone, diisopropyl adipate, alcohol, C12-15 alkyl lactate, butylated hydroxytoluene, citric acid anhydrous, and disodium edetate.

In another aspect of the invention, a method of treating onychomycosis is provided, the method comprising applying a pharmaceutically acceptable efinaconazole formulation once a day for a treatment period of at least 36 weeks to the treatment area of an onychomycosis patient (a) without debriding the nail or nail-associated tissue in the treatment area initially or during the treatment period, (b) without removing the formulation from the treatment area during the treatment period, and (c) without occluding the treatment area; wherein the efinaconazole formulation comprises 10% w/w efinaconazole, water, cyclomethicone, diisopropyl adipate, alcohol, C12-15 alkyl lactate, butylated hydroxytoluene, citric acid anhydrous, and disodium edetate.

The preceding exemplary aspects are just some of the embodiments of the invention. Additional features of these embodiments and further aspects of the invention will be clear from the remainder of the description of the invention provided here. Further aspects include:

1. A method of treating onychomycosis comprising applying a pharmaceutically acceptable formulation comprising 10% w/w efinaconazole once a day for a treatment period of at least 36 weeks to the treatment area of an onychomycosis patient (a) without debriding the nail or nail-associated tissue initially or during the treatment period and/or (b) without removing the formulation from the treatment area during the treatment period.

2. The method of aspect 1, wherein the method is performed (a) without debriding the nail or nail-associated tissue initially or during the treatment period and (b) without removing the formulation from the treatment area during the treatment period.

3. The method of aspect 1 or aspect 2, wherein the patient waits at least 10 minutes before administering the formulation if the treatment area was previously in contact with water.

4. The method of aspect 1 or aspect 2, wherein the method includes a step of cleaning the treatment area prior to administering the efinaconazole formulation.

5. The method of aspect 1 or aspect 2, wherein the patient cleans the treatment area prior to treatment and waits for at least 10 minutes before administering the formulation if the cleaning includes wetting the treatment area with water.

6. The method of any one of aspects 1-5, wherein the efinaconazole is the only active pharmaceutical ingredient in the formulation.

7. The method of any one of aspects 1-6, wherein the formulation comprises a vehicle that is volatile and/or that rapidly penetrates the nail and a wetting agent.

8. The method of aspect 7, wherein the vehicle is an alcohol and the wetting agent is a volatile silicone.

9. The method of aspect 8, wherein the formulation comprises an amount of butylated hydroxytoluene (BHT), and an amount of a salt of ethylenediaminetetraacetic acid (EDTA), the amounts of BHT and EDTA being sufficient to ensure the composition is (i) colorless upon initial manufacturing of the composition and (ii) colorless or pale yellow after storage for at least three weeks at a temperature of at least about 40° C.

10. The method of any one of aspects 1-9, wherein the treatment period is 48 weeks.

11. The method of any one of aspects 1-10, wherein the method comprises nail cutting on a more frequent than typical basis.

12. The method of any one of aspects 1-10, wherein the method comprises cutting nails once every two weeks or more frequently.

13. The method of any one of aspects 1-10, wherein the method does not comprise cutting nails more often than every two weeks.

14. The method of any one of aspects 1-13, wherein the efinaconazole formulation is not administered in an occluded or semi-occluded manner.

15. The method of any one of aspects 1-14, wherein the method comprises uniformly spreading the efinaconazole formulation throughout the treatment area with an applicator.

16. The method of aspect 15, wherein the average amount of efinaconazole delivered to each $cm^2$ of the treatment area is about 0.15 $mg/cm^2$ to about 0.45 $mg/cm^2$.

17. The method of any one of aspects 1-16, wherein the method comprises administering the efinaconazole formulation from a container that is in fluid communication with an applicator, loading the applicator, and applying the efinaconazole with the applicator.

18. The method of any one of aspects 1-17, wherein performance of the method in a patient population results in a mycological cure rate of at least about 40%, a clinical efficacy rate of at least about 20%, a complete cure rate of at least about 10%, or a combination of any or all thereof. 19. A method for treating onychomycosis comprising applying a pharmaceutically acceptable formulation comprising administering 0.5 mg to 4 mg of efinaconazole to the second toe, third toe, fourth toe, and fifth toe treatment area and administering 1 mg to 8 mg of efinaconazole to the treatment area of the hallux (big toe), the administration comprising manually spreading the efinaconazole with an application device such that the patient does not cause substantial amounts of efinaconazole to come into contact with non-treated areas of the skin and evenly spreading the efinaconazole throughout the treatment area by use of the application device once a day to each treated toe area for a period of at least 36 weeks.

20. The method of any one of aspects 1-19, wherein the efinaconazole formulation is spread uniformly in the target area such that the average amount of efinaconazole delivered to each cm2 of the treatment area is about 0.15 $mg/cm^2$ to about 0.45 $mg/cm^3$.

21. The method of aspect 20, wherein the average concentration of efinaconazole in the nail in a population of patients is about 5500-6000 μg/g after about 14 days of treatment.

22. The method of any one of aspects 1-20, wherein the mean plasma $C_{max}$ in a population of at least 15 adult onychomycosis patients receiving the method after 28 days of treatment is less than 1.9 ng/mL.

23. A method for treating onychomycosis comprising (a) providing a container that is suitable for storing an efinaconazole formulation for pharmaceutical use that comprises an applicator that is capable of dispensing a pharmaceutically effective dose of an efinaconazole solution and spreading an approximately uniform amount of the efinaconazole formulation to a target area by manual action after loading, (b) loading the applicator with the dose of the efinaconazole formulation, and (c) administering the dose of the efinaconazole formulation to the treatment area of each treated toe by uniform manual spreading.

24. The method of aspect 23, wherein the container is a multiple use container and the method comprises repeating steps (a)-(c) of the method for each toe area in the treatment area once a day for at least 4 weeks.

25. The method of aspect 23 or 24, wherein the method comprises manually loading of the applicator with a dose of the efinaconazole formulation.

26. The method of aspect 25, wherein the container is a squeeze sensitive container and the applicator is a flow through applicator which delivers efinaconazole formulation to the target area when a user applies sufficient pressure on the container.

27. The method of any one of aspects 23-26, wherein the method is performed for at least 36 weeks.

28. The method of aspect 27, wherein the method is performed for 48 weeks.

29. The method of any one of aspects 23-28, wherein the applicator is selected from the group consisting of a brush, a pad, a swab, a sponge, or a roller.

30. The method of any one of aspects 23-29, wherein the volume of formulation contained in the applicator is about 75 to about 150 microliters.

31. The method of any one of aspects 23-30, wherein the patient or healthcare worker administering the formulation does not contact his or her hands with a substantial amount of efinaconazole formulation in the performance of the method.

32. A method for treating onychomycosis comprising applying a pharmaceutically acceptable formulation comprising 0.5 mg to 4 mg of efinaconazole to any second toe, third toe, fourth toe, and/or fifth toe in a treatment area of an onychomycosis patient and administering 1 mg to 8 mg of efinaconazole to any hallux (big toe) in the treatment area once a day for a period of at least 36 weeks.

33. The method of aspect 32, wherein the method comprises administering 0.8 mg to 3.7 mg of efinaconazole to any second, third, fourth, and/or fifth toe(s) in the treatment area and 1.6 mg to 7.4 mg efinaconazole to any hallux in the treatment area.

34. The method of aspect 33, wherein the method comprises administering 1.25 mg to 3.25 mg efinaconazole to any second, third, fourth, and/or fifth toe(s) in the treatment area and 2.5 mg to 6.5 mg to any hallux in the treatment area.

35. The method of aspect 34, wherein the method comprises administering 1.4 mg to 2.6 mg efinaconazole to any second, third, fourth, and/or fifth toe(s) in the treatment area and 2.8 mg to 5.2 mg to any hallux in the treatment area.

36. The method of any one of aspects 32-35, wherein the treatment period is 48 weeks.

37. The method of any one of aspects 32-36, wherein the efinaconazole formulation is not administered in an occluded or semi-occluded fashion.

38. The method of any one of aspects 32-36, wherein the method does not comprise debriding the nail or nail-associated tissue prior to or during treatment.

39. The method of any one of aspects 32-36, wherein the method does not comprise the step of removing the formulation from the treatment area during the course of treatment.

40. The method of any one of aspects 32-39, wherein the method comprises approximately uniformly administering the efinaconazole formulation to the treatment area by manual application with an applicator.

41. The method of aspect 40, wherein the applicator is a flow-through brush applicator.

42. A method for treating onychomycosis comprising applying a pharmaceutically acceptable formulation comprising administering a pharmaceutically acceptable 8-15% efinaconazole formulation to a treatment area of an onychomycosis patient once a day for at least 36 weeks in a manner such that the concentration of efinaconazole in the nail is between 5000 μg and 9000 μg per gram of sample toenail tissue analyzed.

43. The method of aspect 42, wherein the average concentration of efinaconazole in the nail in a population of patients is about 5500-6000 μg/g after about 14 days of treatment.

44. A method of treating onychomycosis comprising applying a pharmaceutically acceptable formulation comprising 10% efinaconazole once a day for a treatment period at least 36 weeks to the treatment area of an onychomycosis patient in a treatment regimen that results in a mean plasma $C_{max}$ in a population of at least 15 adult onychomycosis patients after 28 days of treatment is less than 1.9 ng/mL.

45. The method of aspect 44, wherein the mean plasma $C_{max}$ in a population of at least 15 adult onychomycosis patients after 28 days of treatment is less than 1.5 ng/mL.

46. The method of aspect 45, wherein the mean plasma $C_{max}$ in a population of at least 15 adult onychomycosis patients after 28 days of treatment is less than 1 ng/mL.

47. The method of aspect 46, wherein the mean plasma $C_{max}$ in a population of at least 15 adult onychomycosis patients after 28 days of treatment is less than 0.8 ng/mL.

48. The method of aspect 47, wherein the mean $C_{max}$ in a population of onychomycosis patients receiving the treatment is between 0.55-0.725 ng/mL.

49. The method of aspect 48, wherein the mean plasma $C_{max}$ in the patient population is 0.67 ng/mL.

50. A method of treating onychomycosis comprising applying a pharmaceutically acceptable formulation comprising 10% efinaconazole once a day for a treatment period at least 36 weeks to the treatment area of an onychomycosis patient in a treatment regimen that in a population of healthy patients results in an efinaconazole plasma half-life of 25-35 hours.

51. The method of aspect 50, wherein the plasma half-life of the efinaconazole in a patient population treated with the efinaconazole formulation is about 29.9 hours.

52. A method of treating onychomycosis comprising applying a pharmaceutically acceptable formulation comprising 10% efinaconazole once a day for a treatment period at least 36 weeks to the treatment area of an onychomycosis patient such that the $C_{max}$ after 28 days of treatment is less than 8 ng/mL.

53. A method of treating onychomycosis comprising applying a pharmaceutically acceptable formulation comprising 10% efinaconazole once a day for a treatment period at least 36 weeks to the treatment area of an onychomycosis patient in a treatment regimen that results in a mean area under the curve (AUC) in a population of at least 15 adult onychomycosis patients after 28 days of treatment of between about 5 and about 20 ng*h/mL.

54. A device for treating fungal infections comprising (a) a container portion that securely holds a flowable pharmaceutical formulation of efinaconazole and that can maintain the formulation in a pharmaceutically acceptable state for extended periods of time at room temperature and (b) a loading portion that is capable of being loaded with a desired dose of the efinaconazole formulation when a user desires to apply a treatment, and (c) means for delivering the dose of the efinaconazole formulation by manual application evenly across the treatment area of a toe.

55. The device of aspect 54, wherein the formulation is a liquid.

56. The device of aspect 54, wherein the formulation is a gel or a lotion.

57. The device of any one of aspects 54-56, wherein the delivery means comprises a brush.

58. The device of aspect 57, wherein the device is flow-through brush cap that other than the brush seals or selectively seals the container.

59. The device of any one of aspects 54-57, wherein the delivery means is a flow through applicator.

60. The device of aspect 59, wherein the container portion is squeezable and the applicator is loaded by manual application of pressure to the container.

61. The device of any one of aspects 54-60, wherein the device comprises means for enclosing the delivery means.

62. The device of any one of aspects 54-61, wherein the enclosing means is suitable for use for at least 4 weeks.

63. The device of aspect 63, wherein the enclosing means is suitable for 48 weeks of treatment.

64. The device of any one of aspects 54-63, wherein the efinaconazole has a surface tension that is sufficiently low that the formulation can be uniformly spread to all portions of a toenail or fingernail treatment area quickly and with minimal manual effort.

65. A pharmaceutical formulation comprising 10% w/w efinaconazole, 13% cyclomethicone, 12% diisopropyl adipate, C12-15 alkyl lactate, 1% water, over 50% alcohol, and sufficient amounts of BHT, citric acid, and a salt of EDTA to maintain the color stability of the formulation.

DETAILED DESCRIPTION OF THE INVENTION

Figure 1:
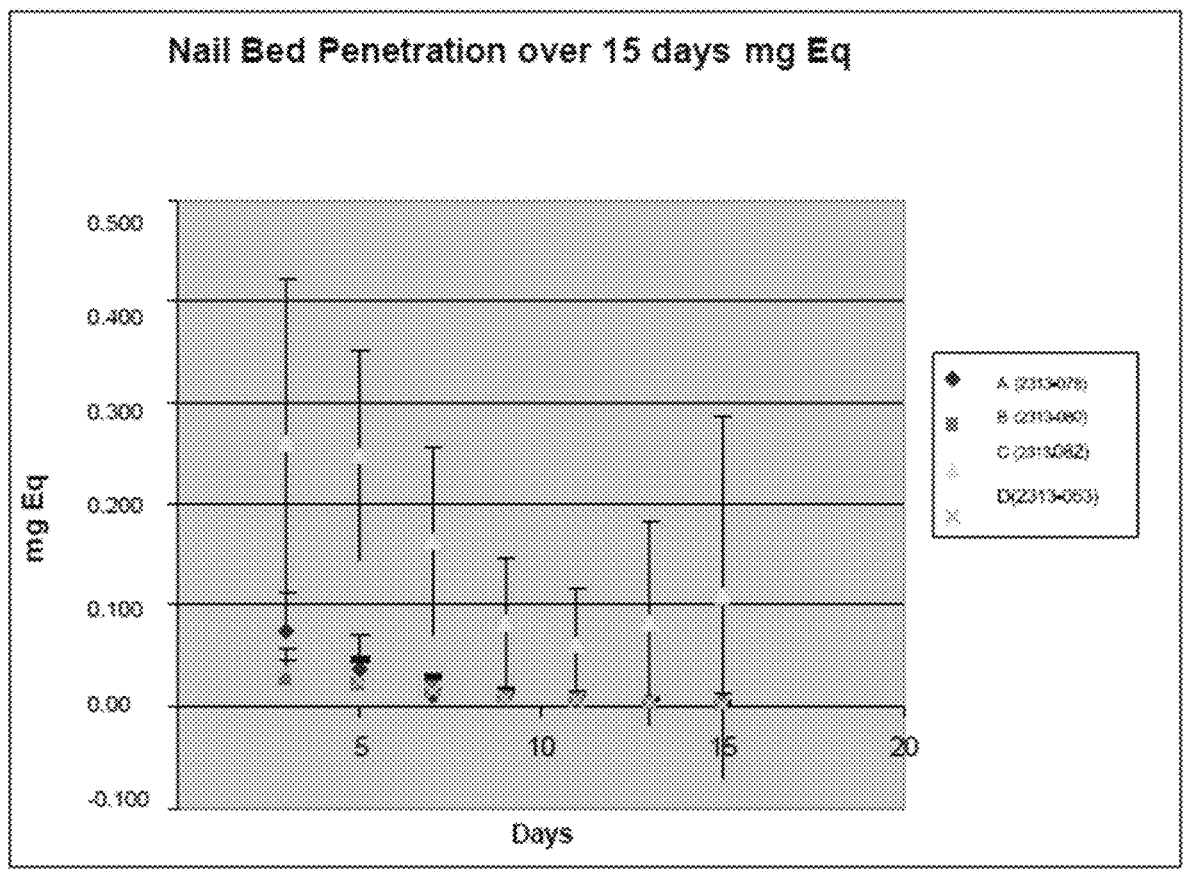
FIG. 1 shows the amount of efinaconazole penetrated through the nail into receptor phase (cotton ball wetted with saline), exhibited during preclinical studies. Sampling on days 3, 5, 7, 9, 11, 13 and 15.

In one aspect, the invention provides a method of treating onychomycosis comprising applying a pharmaceutically acceptable formulation comprising 7.5-15% w/w efinaconazole (((2R,3R)-2-(2,4-difluorophenyl)-3-(4-methylenepiperidin-1-yl)-1-(1H-1,2,4-triazol-1-yl) butan-2-ol)), such as 7.5-12.5% w/w efinaconazole, 8-13% w/w efinaconazole, 8.5%-11.5% w/w efinaconazole, 9-11% w/w efinaconazole, and typically about 10% w/w efinaconazole (e.g., 10.0% efinaconazole), once a day, for a treatment period of at least 36 weeks (e.g., 38 weeks, 39 weeks, 40 weeks, 42 weeks, 44 weeks, 46 weeks, or 48 weeks), to the treatment area of an onychomycosis patient (a) without debriding the nail or nail-associated tissue initially or during the treatment period and/or (b) removing the formulation from the treatment area during the treatment period. Efinaconazole has been described in a number of patent documents and publications (see, e.g., U.S. Pat. Nos. 5,620,994 and 7,214,506). For convenience, the chemical structure of efinaconazole is shown below:

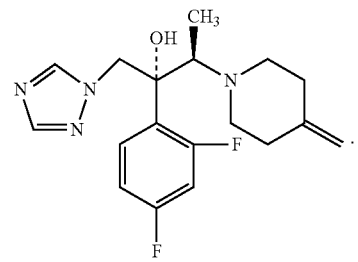

Molecular Formula : $C_{18}H_{22}F_2N_4O$
Molecular Weight: 348.39

In some embodiments, it is particularly advantageous to treat for 48 weeks or longer. The treatment period may be followed by an observation period of 2, 3, or 4 weeks, or longer. In some embodiments, the invention includes a 48 week treatment regimen and a 4 week observation period. In some embodiments, the period of treatment and observation is selected such that the complete cure rate in a population of onychomycosis patients treated for the treatment period once-a-day with the efinaconazole formulation is at least 10% or higher (such as at least 12%, at least 14%, or higher).

The treatment area for an individual nail typically includes the nail, the nail folds, nail bed, hyponychium, and an approximately corresponding area of the undersurface of the nail plate. Typically in performance of the method all of these areas are completely covered with the formulation, which typically is spread in an approximately uniform matter, usually in a thin layer. Typically the treatment area or target area includes less than all of the nails of the patient. For example, the target area might include 2, 3, 4, 5, or 6 nails (e.g., 1 or 2 great nails, and 1-4 small (other) nails). In some cases, however, all the toenails and/or all the fingernails can be affected by onychomycosis. Moreover, in some embodiments all of the nails of a hand or foot in which a visibly affected nail is present are treated. In some embodiments, all of the nails of the feet are treated where there is only one or more visibly affected nail(s) on a single foot. In a similar but distinct embodiment, all of the nails of a hand can be treated where there is no visibly affected nails where there is one or more visibly affected nails on the other hand and/or all of the nails of a hand may be treated even though only one or less than all of the nails on that hand are visibly affected by onychomycosis.

Onychomycosis is a relatively well understood disorder and, accordingly, is not described in significant detail here. Typically treatment of onychomycosis in the context of the methods described here includes treatment of tinea unguium. Efinaconazole has been demonstrated to be effective against a number of disease-causing agents associated with onychomycosis.

In certain embodiments, the invention provides a method in which no debriding of the nail and/or nail-associated tissue occurs as part of the method. Debridement often has been required in the treatment of onychomycosis, particularly in association with previously known topical anti-onychomycosis drugs. Methods provided herein do not require such actions. It also should be understood that many methods provided herein do not require avulsion (removal) of all or substantially the entire infected nail, which is another practice that has been employed in treating onychomycosis.

Debridement in the context of onychomycosis can take many forms and the term is generally used herein in the manner that those of ordinary skill in the art would use without any other limitation. Often, debriding in the context of onychomycosis treatments is viewed as the process of removing infected tissue or tissue associated (located closely to) infected tissue or tissue to be treated by administration of the efinaconazole formulation.

Those of skill the art will appreciate the significant advantages provided by the methods of the invention, including the absence of requirements for burdensome techniques such as occlusion and debridement. In general, debridement by mechanically reducing or otherwise reducing nail thickness to remove onychomycotic or potentially infected material, usually through repeated application, can be avoided. Thus, for example, the invention can be characterized by not requiring a step of scraping, aggressive clipping, and/or filing the nail down, all of which are examples of possible mechanical debridement strategies not practiced in connection with the therapeutic methods provided herein.

Typically, debridement via clipping of infected nails with frequency that is greater than ordinary clipping (e.g., clipping about every two weeks or more frequently, every 10 days or more frequently, about every week or more frequently, every 5 days or more frequently, every 3 days or more frequently, or clipping about every day or every day) is also avoided by using the methods of the invention. Debridement by clipping also or alternatively can mean clipping infected and/or treated nails and/or nail-associated tissues more frequently than non-infected nails and/or clipping in a more rigorous manner (e.g., in terms of area clipped, etc.) than is normally performed by the individual being treated or by the average person in the population. Debridement can also comprise, consist essentially of, or be limited to the removal of nail tissue by filing and/or by clipping prior to administration and/or repeat administration of the efinaconazole composition. It should be understood that the invention provides onychomycosis treatment methods in which some or all of these steps (e.g., single debridement or repeated debridement by filing and/or clipping) are excluded from the efinaconazole formulation treatment regimen.

Despite the fact that methods of the invention generally do not include aggressive clipping, it also should be understood that methods of the invention can include the step of clipping nails at a typical rate, a slightly enhanced rate (e.g., 125% as frequently, 150% as frequently, or 200% as frequently), or enhanced rate and/or manner, such as clipping at least about every 3 weeks or at least about every 4 weeks, or even more frequently (e.g., about every 2 weeks or more frequently, about every week or more frequently, about every 5 days or more frequently, about every 3 days or more frequently, or about once a day or daily). Often the patient will be instructed to clip unaffected nails before affected nails, to clean the nail clipper after each use, and to not share the clipper with any other person in such cases.

Removal of an anti-onychomycosis formulation (or medicine or medicament) is also regularly practiced in connection with previously described topical therapies for the condition. Removal can be by simple mechanical wiping or any other cleaning of the surface/area that was contacted with the treatment formulation and/or by contacting the treated area with a chemical agent that removes the drug. The invention provides methods in which no form of removal is required as part of the treatment regimen. The formulation is allowed to stay on the treatment area without any kind of active removal on the part of the patient or other individual. As a result, efinaconzole will often remain in nail tissue or surrounding tissue for the majority of the treatment period, including up to the entirety of the treatment period.

In some embodiments, the invention provides treatment methods in which neither debridement nor removal of the formulation used to treat the onychomycosis is required.

The efinaconazole formulation is generally applied by a patient or healthcare professional to a treatment area. A treatment area can include one or more "small" toes (the second, third, fourth, and/or fifth toes) on one or both feet and/or the hallux ("big toe") on one or both feet. Thus, if the hallux, first toe, and second toe on the right foot of a patient are exhibiting onychomycosis and the fourth and fifth toe of the left foot are exhibiting onychomycosis these five toes make up the treatment area. The more specific treatment area of each toe is typically made up of the infected toenail and surrounding tissue. In some cases, the method is used to also or alternatively treat onychomycosis of the fingernails in which case the specific treatment area of a finger would include the infected fingernail and associated surrounding tissue. In such cases the treatment area would typically be understood to include both the infected fingers and toes; however in some cases distinctions might be made between these different treated body parts (e.g., by specifying a hand treatment area and a foot treatment area). The same can be true of different infected feet (e.g., it may be useful to define a left foot treatment area and right foot treatment area), although unless it is specified the treatment area should be considered to be the entire area of the onychomycosis patient detectably exhibiting the disease.

Typically, the methods of the invention will include cleaning the treatment area prior to application of the efinaconazole formulation. Cleaning can be by any suitable means and no special type of cleaning is required. Typically cleaning means removal of dirt and debris based on visual inspection. Cleaning may be associated with instructions and/or training provided to the patient for performance of the treatment regimen.

If the treatment area has been in contact with water prior to treatment, either due to the above-mentioned cleaning step or otherwise, a short time period (typically at least 10 minutes) should be provided before contacting the treatment area with the efinaconazole formulation. Thus, the invention provides methods wherein the method comprises the step of administering the efinaconazole formulation to the skin of a patient that has not been wetted or wet for at least 10 minutes prior to contact with the formulation. In some embodiments, the cleaning step comprises washing the treatment area with water prior to treatment and waiting at least 10 minutes before applying the efinaconazole formulation.

In some embodiments, the method comprises the administration of one or more additional therapies as part of the treatment. The additional therapies can include application of mechanical therapies or administration of additional therapeutic agents (e.g., an additional topical agent and/or additional oral agent). In some embodiments, efinaconazole is the only anti-onychomycosis agent administered to the patient during the treatment period. In some embodiments, efinaconazole is the only anti-fungal agent administered during the treatment period. In some embodiments, efinaconazole is the only active pharmaceutical ingredient administered to the patient during the treatment period or as part of the treatment altogether.

The efinaconazole formulation can be any suitable formulation for delivering the efinaconazole to the treatment area and treating onychomycosis. In certain embodiments, the formulation is selected and/or adjusted to provide delivery of a particular amount of efinaconazole to the patient, the treatment area, or a subset of the treatment area (e.g., to one or more nails in the treatment area).

In certain embodiments, the formulation comprises (a) a vehicle that is volatile and/or rapidly penetrates the nail and/or (b) a wetting agent. Typically the formulation will both comprise a volatile and/or rapidly penetrating vehicle and a wetting agent. The vehicle can be any suitable vehicle. In some embodiments, the vehicle is an alcohol. In some embodiments, the wetting agent is a volatile silicone. The formulation typically also includes a non-volatile solvent in which the efinaconazole is dissolved, suspended, dispersed, or emulsified (the efinaconazole also can be dissolved, suspended, dispersed, or emulsified in both the volatile and non-volatile solvent or a mixture thereof). The wetting agent and the vehicle can be the same ingredient. Such a pharmaceutical composition typically has a surface tension of 40 dynes/cm or less. In a preferred embodiment, 35 dynes/cm or less, 30 dynes/cm or less, or 25 dynes/cm or less. Typically, the composition is free of film forming compounds, such as polymers and copolymers of polyvinyl acetate, polyvinylpyrrolidone, methacrylic acid, polyvinyl butyrals, polyvinyl acetals, and cellulose derivatives such as cellulose acetate phthalate, cellulose acetate butyrate, cellulose acetate propionate, cellulose nitrate, cellulose sulfate, ethylcellulose, and cellulose acetate. A polymeric film forming agent typically is only present in the composition if it is present as a type and/or in an amount below that which will result in the formation of a solid film or lacquer following application of the composition to the surface of a nail.

The formulation typically is capable of rapidly penetrating the nail. Penetration in this context means that the after about 10 minutes following application of a thin layer of the vehicle onto the surface of a nail, no more than about 85%, such as no more than about 60%, more particularly no more than about 55% or no more than about 50% of the applied amount remains on the nail surface.

The formulation typically is a solution. The formulation generally is not a lacquer. The formulation typically also is not an enamel, a varnish, or a polish. The formulation is typically clear and/or colorless. The formulation generally does not form a film in that it does not create a solid film layer that is detectable for a significant period of time, such as after about 4 hours, 6 hours, 8 hours, 12 hours, 18 hours, 24 hours, 30 hours, 36 hours, or 48 hours. Methods also or alternatively can be characterized in that practice of the method does not result in a layer that is required to be or even can be peeled off or scraped off by manual action. Examples of formulations useful in the practice of methods provided herein are provided in U.S. Pat. No. 8,039,494 ("the '494 patent"), which is incorporated in its entirety herein.

In some embodiments, the composition comprises efinaconazole, a volatile alcohol, a volatile silicone, an antioxidant, and one or more esters of the formula RCO—OR', wherein R and R' may be identical or different and each of R and R' represents a linear or branched chain of an alkyl, alkenyl, alkoxycarbonylalkyl, or alkoxycarbonyloxyalkyl radical having from 1 to 25 carbon atoms, and wherein the chain of R' is at least 5 carbons, wherein the volatile silicone is present in the composition at a concentration less than 25% w/w, wherein the composition does not form a solid film when topically applied to the surface of a nail, and wherein the surface tension of the composition is 40 dynes/cm or less.

In some embodiments, the composition comprises efinaconazole, a volatile alcohol, a volatile silicone, an antioxidant, and one or more esters of the formula RCO—OR', wherein R and R' may be identical or different and each of R and R' represents a linear or branched chain of an alkyl, alkenyl, alkoxycarbonylalkyl, or alkoxycarbonyloxyalkyl radical having from 1 to 25 carbon atoms, and wherein the chain of R' is at least 5 carbons, wherein the ratio of alcohol to volatile silicone in the composition % w/w is at least 2:3, wherein the composition does not form a solid film when topically applied to the surface of a nail and wherein the surface tension of the composition is 40 dynes/cm or less.

As used herein, the term "volatile" when referring to the vehicle means that the vehicle is a compound that evaporates from the surface of the nail when applied. Volatile vehicles are compounds which have a measurable vapor pressure, and preferably are compounds that have a vapor pressure of greater than about 100 Pa at room temperature. Examples of volatile vehicles include: acetone, 2-amino-2-methyl-1-propanol, 1,2-butanediol, 1, 4-butanediol, 2-butanol, cyclomethicone-4, cyclomethicone-5, cyclomethicone-6, ethanol, ethyl acetate, n-heptane, isobutanol, isopropyl alcohol, 1-propanol, 2-propanol, and water.

As used herein, the term "penetrating" when referring to the vehicle means that the vehicle is a compound that rapidly penetrates into a nail when applied to the surface of the nail so that, after 10 minutes following the application of a thin layer of the vehicle onto the surface of a nail, no more than 10% of the applied amount remains on the nail surface. The term penetrating thus includes both volatile and non-volatile vehicles.

Volatile silicones include linear or cyclic polyorganosiloxane compounds of formula $[R_1SiOR_2]_n$, wherein n=6 or less and $R_1$ and $R_2$ are alkyl groups that may be the same or different, and which compound has a measurable vapor pressure under ambient conditions. Preferably, n=from 3 to 6, and most preferably n=4 or 5. Preferably $R_1$ and R₂=methyl. Examples of cyclic volatile silicones include polydimethylcyclosiloxanes, generally known as cyclomethicones. Particular examples of cyclic volatile silicones include cyclopentasiloxane, cyclotetrasiloxane, decylmethylcyclopentasiloxane, and octylmethylcyclotetrasiloxane. Examples of linear volatile silicones include linear polysiloxanes. Particular examples of linear volatile silicones include hexamethyldisiloxane, octamethyltrisiloxane, and dimethicones.

In some embodiments, the ester is a combination of diisopropyl adipate and C12-15 alkyl lactate. In some embodiments, the ester is a combination of diisopropyl adipate and myristyl lactate.

In some embodiments, the alcohol is ethanol. In some embodiments, the volatile silicone is a cyclic silicone. In some embodiments, the cyclic silicone is a cyclomethicone. In some embodiments, the concentration of volatile silicone is less than 20%. In some embodiments, the concentration of volatile silicone is less than 15%.

In some embodiments, the ratio of alcohol to volatile silicone is at least 1:1. In some embodiments, the ratio of alcohol to volatile silicone is at least 2:1. In some embodiments, the ratio of alcohol to volatile silicone is at least 3:1.

In some embodiments, the composition comprises efinaconazole, alcohol, cyclomethicone, diisopropyl adipate, either or both of C12-15 alkyl lactate and isopropyl myristate, and an antioxidant.

In some embodiments, the composition comprises the following components in the following ranges of concentrations % w/w:
 a. alcohol—10% to 80%
 b. cyclomethicone—0.01% to less than 25%
 c. diisopropyl adipate plus either or both of C12-15 alkyl lactate and isopropyl myristate—5% to 90%
 d. antioxidant—0.001% to 0.50%
 e. efinaconazole—0.0001% to 30%.

In some embodiments, the composition comprises:
 a. alcohol—50% to 70%,
 b. cyclomethicone—10% to 15%
 c. diisopropyl adipate—8% to 15%
 d. either or both of C12-15 alkyl lactate and isopropyl myristate—8% to 15%
 e. antioxidant—0.001% to 0.50%
 f. efinaconazole—2% to 15%.

As used herein, the term "surface tension" refers to the force required to increase unit area of a surface of a liquid or of an interface between two liquids or between a liquid and a gas, generally stated in units of dynes/cm. Surface tensions described herein are measured by the Du Noüy ring method utilizing an EasyDyne tensiometer model K20 marketed by Krüss USA, Matthews, N.C.

The composition has a surface tension that is sufficiently low so that, when the composition is applied to the surface of a toenail on a human subject, the composition spreads into the nail folds and also is wicked into the gap between the nail and the nail bed if such a gap is present. A gap is generally present in a nail that is suffering from a disorder such as onychomycosis. Preferably, the surface tension of the composition is 40 dynes/cm or less, more preferably 35 dynes/cm or less, even more preferably 30 dynes/cm or less, and most preferably, the surface tension is 25 dynes/cm or less.

It is preferred that the composition, when applied to the surface of a nail, does not form a solid film or lacquer and it is most preferred that the composition is free of polymeric film forming compounds. Examples of polymeric film forming compounds include polymers and copolymers of polyvinyl acetate, polyvinylpyrrolidone, methacrylic acid, polyvinyl butyrals, polyvinyl acetals, and cellulose derivatives such as cellulose acetate phthalate, cellulose acetate butyrate, cellulose acetate propionate, cellulose nitrate, cellulose sulfate, ethylcellulose, and cellulose acetate. A polymeric film forming agent may be present in the composition of this application if it is present in an amount below that which will result in the formation of a film or lacquer following application of the composition to the surface of a nail.

The spreadability of a composition may be defined by a test such as the single slide spreadability test, which may be performed as follows. One hundred microliters of a test formulation is applied to a single point on the surface of a clean dry single glass slide. The area of spread of the formulation on the glass slide is determined at various times following the application, such as at 1, 2, 4, 6, and 10 minutes. Formulations that are most suitable for the present method continue to spread on the surface of the slide throughout the first 6 minutes and preferably throughout the first 10 minutes. Preferably, but not necessarily, the area of coverage of the formulation on the slide after 10 minutes is higher than 11.0 cm².

In some embodiments, the composition does not comprise a polymeric film forming compound.

In some embodiments, the composition increases in spread on the surface of a clean dry glass slide throughout the six-minute period immediately following application of the composition to the surface of the slide. In some embodiments, the spread of the composition on the surface of the slide encompasses an area of greater than 11.0 cm within 10 minutes following application of 100 microliters of the composition to the surface of the slide.

In some embodiments, the surface tension of the composition is 35 dynes/cm or less. In some embodiments, the surface tension of the composition is 30 dynes/cm or less. In some embodiments, the surface tension of the composition is 25 dynes/cm or less.

The formulation can include any suitable number, type, and combination of excipients, examples of which are described in the '494 patent. In certain embodiments, the formulation includes an amount of butylated hydroxytoluene (BHT) and an amount of a salt of ethylenediaminetetraacetic acid (EDTA), the amounts of BHT and the salt of EDTA being sufficient to ensure the composition is (i) colorless upon initial formulation and (ii) colorless or pale yellow after storage for at least three weeks at a temperature of at least about 40° C. Often the formulation also will contain citric acid, which may further aid in color stabilization of the formulation. The amount of these excipients required for color stabilization can be relatively small, for example, the formulation may include about 0.2% citric acid or less, such as 0.1% w/w citric acid, anhydrous; 0.0005% or 0.0003% EDTA salt (such as 0.00025% edetate disodium); and 0.2% or 0.1% BHT. Examples of such formulations are described in U.S. Provisional Patent Application No. 61/886,569 ("the '569 provisional", the entirety of which is hereby incorporated for all purposes.

Compositions of the invention can contain butylated hydroxytoluene (BHT) in an amount that, in combination with the amount of EDTA in the composition, is capable of maintaining color stability of the efinaconazole composition such that after a period of three weeks, one month, or longer, even at relatively high temperatures (e.g., about 40° C., about 50° C., about 60° C., about 65° C., or higher) the composition maintains a colorless or pale yellow color, as determined by visual inspection, UV-visual spectrum data, or other suitable color measurement methods. The amount of BHT can vary with the amount of EDTA present, the amount of efinaconazole, and the nature of the composition and the other components of the composition. The compositions can contain, for example, from about 0.01% to about 2% BHT, from about 0.01% to about 1% BHT, from about 1% to about 2% BHT, from about 0.5% to about 1.5% BHT, or from about 0.75% to about 1.25% BHT. In some embodiments, the compositions contain about 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.00%, 1.05%, 1.10%, 1.15%, 1.20%, 1.25%, 1.30%, 1.35%, 1.40%, 1.45%, 1.50%, 1.55%, 1.60%, 1.65%, 1.70%, 1.75%, 1.80%, 1.85%, 1.90%, 1.95%, or about 2.00° A BHT by weight.

The compositions can contain a salt of ethylenediaminetetraacetic acid (EDTA). The salt of ethylenediaminetetraacetic acid can be any suitable salt. Typically the salt will be one that is acceptable for pharmaceutical formulations and compatible with efinaconazole.

Frequently used salts are the disodium and tetrasodium salts of ethylenediaminetetraacetic acid. The amount of EDTA can be any amount that in combination with the amount of BHT provides a colorless composition on initial formulation and maintains a colorless to pale yellow formulation at relatively high temperatures (e.g., at least about 40, at least about 50, or at least about 60° C.) for periods of at least about 3 weeks (e.g., at least about 4 weeks, at least about 6 weeks, at least about 8 weeks, at least about 10 weeks, at least about 12 weeks, at least about 4 months, at least about 6 months, or longer). Typically compositions will contain from about 0.0001° A to about 1° A EDTA. The amount of EDTA used will vary depending on factors including the amount of efinaconazole, the amount of BHT, and the nature of the formulation. For example, in a gel formulation the amount of EDTA used typically will be higher than the amount used in a solution. Also, the amount of EDTA that is used in a non-aqueous formulation or low water content formulation can be lower than the amount of EDTA that is used in a formulation with higher water content. Thus, in one example, the amount of EDTA in a composition of the invention is between about 0.1% and about 1% by weight (e.g., about 0.2%-1%, about 0.25-0.75%, about 0.3-0.8%, or about 0.4-0.7%, such as 0.15%, 0.35%, 0.45%, 0.5%, 0.6%, 0.7%, or 0.9%). Such amounts are useful in, e.g., gel compositions. In other compositions the amount of EDTA is in the range of about 0.004% or about 0.005% to about 0.2%, such as about 0.175%, about 0.15%, about 0.125%, or about 0.1%. The inventors also have surprisingly found that in certain formulations the amount of EDTA can be in the range of only about 0.0001% EDTA to about 0.0005% EDTA, such as from about 0.0001% to about 0.00025% EDTA, from about 0.00025% to about 0.00050% EDTA, or from about 0.0002% to about 0.0004% EDTA. In particular embodiments, the compositions contain about 0.00010%, 0.00012%, 0.00014%, 0.00016%, 0.00018%, 0.00020%, 0.00022%, 0.00024%, 0.00026%, 0.00028%, 0.00030%, 0.00032%, 0.00034%, 0.00036%, 0.00038%, 0.00040%, 0.00042%, 0.00044%, 0.00046%, 0.00048%, or about 0.00050% EDTA by weight. In particular embodiments, the amount of EDTA included in the composition is in the range of about 0.0001% (w/w) to about 0.0005% (w/w) (e.g., 0.0002% or 0.0004%) and the amount of BHT is in the range of about 0.01% (w/w) to about 2% (w/w) (e.g., 0.02%, 0.04%, 0.05%, 0.07%, 0.08%, 1.0%, 1.2%, 1.4%, 1.5%, 1.7%, or 1.9%).

In some exemplary embodiments, the amount of EDTA is in the range of about 0.0001% (w/w) to about 0.0005% (w/w) and the amount of BHT is in the range of about 0.01% (w/w) to about 2% (w/w). In some exemplary embodiments, the amount of EDTA is in the range of about 0.0001% (w/w) to about 0.0003% (w/w) the amount of BHT is in the range of about 0.05% (w/w) to about 0.15%. In other exemplary embodiments, the amount of EDTA is in the range of about 0.1% to about 1.0% by weight (e.g., about 0.15% w/w to about 0.75% w/w), the amount of BHT is in the range of about 0.01% (w/w) to about 2% (w/w) (e.g., about 0.02% or 0.025% to about 1.0% or 1.5% w/w), and the amount of efinaconazole is the range of about 0.5% (w/w) to about 5% (w/w) (e.g., about 1%, about 2%, or about 3%). In still other exemplary embodiments, the amount of EDTA is about 0.00025% (w/w) and the amount of BHT is about 0.1% (w/w).

The amount of citric acid can be any amount that when combined with the EDTA and BHT either results in acceptable color stability, while usually also providing a detectable anti-oxidant effect, or that preferably enhances the color stability of the composition over the color stabilizing effects of BHT and EDTA alone. The compositions can contain, for example, from about 0.01% citric acid to about 1% citric acid by weight. The compositions can contain from about 0.02% to about 0.5% citric acid, from about 0.05% to about 1.5% citric acid, from about 0.08% to about 0.8% citric acid, or from about 0.085% to about 0.5%, 0.4%, 0.3%, or 0.1% citric acid. In some embodiments, the compositions contain about 0.05%, 0.06%, 0.07%, 0.08%, 0.09%, 0.10%, 0.12%, 0.15%, 0.17%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, or about 1.00% citric acid by weight. As for BHT and EDTA, ordinarily skilled formulation scientists will be capable of determining appropriate amounts of citric acid to include in any particular efinaconazole composition given the guidance provided here with respect to color stability.

In some embodiments, the composition contains: from about 0.5% to about 15% efinaconazole by weight, such as from about 0.75% to about 12% efinaconazole by weight (e.g., about 1-5% or about 5-10% efinaconazole by weight), from about 0.01% to about 2% BHT by weight (e.g., about 0.2% to about 1.5% BHT by weight), and from about 0.0001% to about 1.5% EDTA by weight (e.g., about 0.0001% to about 0.0005% EDTA by weight or about 0.1% to about 1.25% EDTA by weight), and about 0.1% to about 1% citric acid by weight.

In some exemplary embodiments, the composition contains: from about 0.5% to about 15% efinaconazole by weight, from about 0.01% to about 2% BHT by weight, from about 0.0001% to about 0.0005% EDTA by weight, and from about 0.1% to about 1% citric acid by weight.

In some exemplary embodiments, the composition contains from about 0.5% to about 15% efinaconazole by weight, about 0.1% BHT by weight, and about 0.00025% EDTA by weight. In some embodiments, the composition further contains about 0.1% citric acid by weight. In some exemplary embodiments, the composition contains from about 0.5% to about 15% efinaconazole by weight, about 0.1% BHT by weight, about 0.00025% EDTA by weight, and about 0.1% citric acid by weight.

The above-described excipients can be in any suitable amounts and/or combinations to provide the features of the composition that are desired (e.g., penetration, spreadability, color stability, PK characteristics, and/or nail absorption, etc.). Suitable quantities for most of the excipients described herein and other excipients that can be in the composition are exemplified in the '894 patent and the '569 provisional.

Typical excipients in an efinaconazole formulation include water, cyclomethicone, diisopropyl adipate, alcohol, C12-15 alkyl lactate, butylated hydroxytoluene, citric acid anhydrous, and disodium edetate.

In some embodiments, the invention also or alternatively provides a method for treating onychomycosis comprising applying a pharmaceutically acceptable formulation comprising 0.35 mg or more (e.g., 0.5 mg, 0.45 mg, or 0.4 mg) to 5 mg or less (e.g., 4 mg, 4.25 mg, 4.5 mg, or 4.75 mg) of efinaconazole to each of any second toe, third toe, fourth toe, and/or fifth toe(s) to be treated in a treatment area of an onychomycosis patient and administering 0.7 mg or more (e.g., 1 mg, 0.9 mg, or 0.8 mg) to 10 mg (e.g., 8 mg, 8.5 mg, 9 mg, or 9.5 mg) of efinaconazole to each of any hallux (big toe) to be treated in the treatment area once a day for a period of at least 36 weeks. In particular embodiments, the invention comprises administering between 0.5 mg and 4 mg efinaconazole to the patient in the treatment.

In some embodiments, the invention comprises administering 0.8 mg to 3.7 mg of efinaconazole to any second, third, fourth, and/or fifth toe(s) in the treatment area and 1.6 mg to 7.4 mg efinaconazole to any hallux in the treatment area.

In some embodiments, the invention provides an onychomycosis treatment method that comprises administering 1.25 mg to 3.25 mg efinaconazole to any second, third, fourth, and/or fifth toe(s) in the treatment area and 2.5 mg to 6.5 mg to any hallux in the treatment area.

In some embodiments, the invention provides a treatment method that comprises administering 1.4 mg to 2.6 mg efinaconazole to any second, third, fourth, and/or fifth toe(s) in the treatment area and 2.8 mg to 5.2 mg to any hallux in the treatment area.

One skill in the art will appreciate that the aspects and embodiments described herein can be combined with each other in various ways. Thus, for example, the invention provides a methods for treating onychomycosis by administering such a total dose of efinaconazole (e.g., about 1.5 mg, such as 1.3-1.7 mg, or about 2 mg, such as 1.7-2.3 mg, to a small toe, and about double the amount to a big toe), once a day, to an onychomycosis, for a treatment period of 38 weeks, 40 weeks, 42, weeks, 44 weeks, 46 weeks, 48 weeks, or longer, wherein the methods do not include any step of debriding the nail and/or periodically removing the residual efinaconazole formulation from the treated area. In certain embodiments, the methods of the invention do not include partially occluding or fully occluding the treatment area to which the efinaconazole is administered. The methods can include a step of cleaning the area before treatment and/or a step of ensuring that at least 10 minutes has passed between the time the treatment area has been wet with water to when administration begins. The cleaning involved with the use of efinaconazole according to this invention generally consists of cleaning practices associated with normal personal hygiene.

In some embodiments, the methods include administration of an efinaconazole formulation, typically having a concentration of efinaconazole (w/w) that is about 10% (e.g., 8-12%, 9-11%, 9.5-10.5%, or 10%), commonly 10%, once a day, for a period of 48 weeks. It has been found that a 48 week treatment period can provide advantages over other treatment periods (e.g., a 36 week treatment period), particularly in connection with administration of a 10% efinaconazole formulation.

Typically, the dose of efinaconazole delivered to each toe is delivered by delivering a volume of efinaconazole formulation of about 75 to about 150 microliters, such as about 90-140 microliters or about 100-130 microliters. The concentration of efinaconazole is generally set to deliver the desired dose (a typical concentration is about 10% w/w). Generally, a relatively set volume, such as a drop from a dropper, is delivered to each small nail treated and a double dose (e.g., two drops) is delivered to each hallux treated. In some cases, there may be delivery of an extra dose to either a small or big toe (or small fingernail or thumbnail in the case of treating a hand infection) such that the dose is slightly higher than intended. Accordingly, the dosages described herein can be viewed as approximations with the understanding that typically a larger amount of the API (and formulation) is delivered to the patient than is intended. For example, a method can include one, two, or three extra drops delivered to the patient to account for such errors in administration, particularly where the method is used in the treatment of patients over 65 years in age, over 70 years in age, over 75 years in age, over 80 years in age, etc., which is a common patient population for onychomycosis treatment.

In some embodiments, the invention provides a method for treating onychomycosis comprising applying a pharmaceutically acceptable formulation comprising administering about 2 g to 10 g efinaconazole formulation to a treatment area of a toenail of an onychomycosis patient in approximately equal daily doses over a period of at least 36 weeks. In some embodiments, the amount of efinaconazole administered to the patient is less than 10 g. The amount of efinaconazole administered to the patient typically will be greater than 2.5 g. Very often the amount of efinaconazole administered to the patient is less than 9 g. Thus, in certain embodiments, the total amount of efinaconazole administered is between about 2.5 and about 9.5 g, such as 2.6 or 2.7 g to 9 g or 9.25 g. In some embodiments, the method involves the administration of 3 g to 9 g efinaconazole to the treatment area (target area) over the treatment period. In some embodiments, the upper end of the range is less than 9 g, such as about 8 g or less, for example about 7 g (e.g., 7.5 g or 7.2 g), or even less (e.g., about 4 g, such as 4.5 g, 4.2 g, 4 g, 3.8 g, 3.75 g, or 3.5 g). In some embodiments, the lower end of the range is below 2 g, such as 1.5 g, 1.75 g, 1.8 g, 1.85 g, or 1.9 g. In certain embodiments, the methods include administering about 3 g to about 9 g (e.g., 3.3 g to 8.8 g) over a 48 week treatment period with a 10% efinaconazole formulation.

In certain embodiments, the methods of the invention are performed with a patient that has previously received efinaconazole treatment. In some embodiments, the invention includes a step of determining if the patient has previously been treated with efinaconazole to determine if the patient has exhibited any sensitivity to or negative response (e.g., local inflammation) to efinaconazole treatment prior to initiating treatment. The patient is generally instructed to only apply the formulation to the nails and immediately adjacent skin (nail-associated tissue). The patient can be advised, for example, that the formulation is not for ophthalmic, oral, or intravaginal use. Typically the patient is counseled about the potential for irritation in the treatment area arising from administration of the formulation and is monitored (self-monitored and/or monitored by a healthcare provider such as a doctor, nurse, etc.) for inflammation during the treatment period to assure that the irritation does not become excessive.

Typically the patient is an adult (e.g., 18 years or older). The patient will often be advised to avoid cosmetic nail products, nail polishes, and pedicures during the treatment period. In some embodiments, the patient is 65 years or older. In some embodiments, the patient is a patient that has one or more risk factors that makes topical treatment of onychomycosis more medically desirable than oral anti-onychomycosis therapy (e.g., risk of and/or history of hepatotoxicity or liver sensitivity/injury and/or risk of drug-drug interactions (DDIs) (e.g., due to undergoing systemic polypharmacy). In some embodiments, the patient is a male. In some embodiments, the patient is also affected by diabetes and/or suffers from a compromised immune system as compared to a typical healthy adult. In certain embodiments, the patient is identified as being at risk of cytochrome inhibition, such as cytochrome P (CYP) inhibition, for example CYP 450 3A4 inhibition, wherein use of oral anti-onychomycosis agents can be problematic or undesirable.

In certain embodiments, the invention also or alternatively provides methods for treating onychomycosis which include applying a pharmaceutically acceptable formulation comprising 8-15% efinaconazole to a treatment area of an onychomycosis patient once a day for at least 36 weeks (e.g., at least 40, 44, or more typically at least 48 weeks) in a manner such that the concentration of efinaconazole in the nail is between about 5000 µg and about 9000 µg per gram of sample toenail tissue analyzed. In some embodiments, methods of the invention are practiced so as to result in a concentration of efinaconazole in a sample of toenail tissue that is between about 5500 µg and about 8500 µg per gram of sample toenail tissue analyzed. In some embodiments, administration results in a concentration of efinaconazole in the nail that is reflected by a concentration of about 5750 µg and about 8000 µg per gram of sample toenail tissue analyzed (e.g., about 5800 µg, about 6000 µg, about 6200 µg, about 6500 µg, about 6800 µg, about 7000 µg, about 7200 µg, or about 7500 µg). These embodiments can be combined with various other embodiments provided herein (unless otherwise stated or clearly contradicted by context).

In some embodiments, the rate of efinaconazole penetration into the nail achieved by performance of methods of the invention can be such that between about 0.02 milligram equivalents (mg Eq) per gram and about 0.7 mg Eq are measured in the nail after 2 weeks of daily administration of the efinaconazole formulation. In certain embodiments, the upper end of the mg Eq range after two weeks of daily administration of the efinaconazole formulation is lower than about 0.7 mg Eq/g, such as about 0.6 mg Eq/g, 0.55 mg Eq/g, 0.5 mg Eq/g, or about 0.45 mg Eq/g (e.g., 0.425 mg Eq/g).

In some embodiments, the invention provides methods for treating onychomycosis comprising applying an amount (such as about 0.5 mg to about 4 mg) of efinaconazole to the second toe, third toe, fourth toe, and fifth toe treatment area and administering approximately twice that amount (e.g., about 1 mg to about 8 mg) of efinaconazole to the treatment area of the hallux (great or "big" toe). Application generally includes manually spreading the efinaconazole with an application device such that the patient does not cause significant amounts of efinaconazole to come into contact with non-treated areas (hands). Application typically includes uniformly spreading the efinaconazole throughout the treatment area by use of the application device such that the average amount of efinaconazole delivered to each $cm^2$ of the treatment area is about 0.15 $mg/cm^2$ to about 0.45 $mg/cm^2$ once a day. In some embodiments, the method comprises administering efinaconazole to an average concentration of about 0.175 $mg/cm^2$ (e.g., about 0.185 $mg/cm^2$) to 0.425 $mg/cm^2$ (e.g., 0.410 $mg/cm^2$, 0.412 $mg/cm^2$, 0.413 $mg/cm^2$, 0.416 $mg/cm^2$, 0.418 $mg/cm^2$, 0.42 $mg/cm^2$, or 0.422 $mg/cm^2$). In some embodiments, the average amount of efinaconazole that is present on the nail upon loading is about 0.25 $mg/cm^2$ (e.g., 0.246 $mg/cm^2$ or 0.248 $mg/cm^2$), 0.3 $mg/cm^2$, or about 0.4 $mg/cm^2$ (e.g., 0.038 $mg/cm^2$), or a range that encompasses these averages (e.g., 0.2 $mg/cm^2$ or 0.24 $mg/cm^2$ to 0.45 $mg/cm^2$ or 0.4 $mg/cm^2$). As loading is typically by manual administration and the treatment area has a large number of different surface types and shapes, these values should be understood as an approximation of the amount that will be delivered on average to the surface of a nail area during treatment by the user attempting to achieve a uniform distribution of the efinaconazole formulation, per typical instructions provided in connection with methods described herein.

The inventive methods typically are employed in a manner to reduce systemic exposure to efinaconazole, which can be reflected in relatively low pharmacokinetic measurements. In some embodiments, the mean plasma $C_{max}$ in a population of adult onychomycosis patients (e.g., at least 10 patients, at least 12 patients, such as 15 patients, or more patients) after 28 days of once a day treatment with an efinaconazole formulation useful for treatment of onychomycosis is less than 2 ng/mL, such as less than 1.9 ng/mL, less than 1.75 ng/mL, less than 1.5 ng/mL, less than 1.33 ng/mL, less than 1.25 ng/mL, or less than 1 ng/mL. In one certain embodiments, the method comprises treating onychomycosis with an efinaconazole formulation that results in a mean plasma $C_{max}$ in a population of at least 15 adult onychomycosis patients after 28 days of once daily treatment that is less than 0.8 ng/mL. In some embodiments, the method is practiced with an efinaconazole formulation that exhibits a $C_{max}$ in a population of onychomycosis patients receiving the treatment once a day that is between 0.55-0.725 ng/mL after 28 days of treatment. In some embodiments, the invention comprises applying an efinaconazole formulation that is associated with a mean plasma $C_{max}$ in a patient population of about 0.65 ng/mL, such as 0.67 ng/mL, after a treatment testing period, such as after 10, 12, 14, 16, 18, 20, 25, or 28 days of treatment.

The methods of the invention also or alternatively can be characterized by resulting in an individual $C_{max}$ after 28 days of treatment that is less than about 10 ng/mL, such as less than about 9 ng/mL, such as less than 8 ng/mL.

In some embodiments, the invention also or alternatively includes applying an efinaconazole formulation that results in an efinaconazole plasma half-life of 25-35 hours when administered for a suitable test period (e.g., 10, 12, 14, 16, 18, 20, 21, 25, 28, 30, or more days). In some embodiments, the half-life in a patient population treated with the formulation is about 30 hours. In certain embodiments, the half-life of the efinaconazole in the patient population is 29.9 hours.

In some embodiments, the invention provides methods of treating onychomycosis including application of an efinaconazole formulation (e.g., a 4-14% efinaconazole formulation, such as a 10% efinaconazole formulation) once a day for a treatment period at least 36 weeks, typically at least 48 weeks, to the treatment area of an onychomycosis patient in a treatment regimen that results in a mean area under the curve (AUC) in a population of adult onychomycosis patients (e.g., at least 10, 12, 15, or more patients) after 28 days of treatment of between about 5 and about 20 ng*h/mL.

In some embodiments, the invention includes the use of an administration device to provide desired distribution of the efinaconazole formulation at the treatment (target) site. Thus, some embodiments of the invention provide methods for treating onychomycosis comprising (a) providing a container that is suitable for storing an efinaconazole formulation for pharmaceutical use that comprises an applicator that is capable of dispensing a pharmaceutically effective dose of an efinaconazole formulation and spreading an approximately uniform amount of the efinaconazole formulation to a target area by manual action after loading (or after filling) (i.e., when loaded), (b) loading the applicator with the dose of the efinaconazole formulation, and (c) administering the dose of the efinaconazole formulation to the treatment area of each affected or treated toe by uniform manual spreading. The formulation in such embodiments is a spreadable composition. Accordingly, the composition is either a liquid or semisolid (e.g., a gel, a cream, an ointment, a lotion, or a liquid suspension, fluid or other suitable liquid).

The container can be any container that is suitable for containing the efinaconazole formulation for intended periods of storage. The container can be made of, for example, a glass or a plastic material. The materials that make up the container should be generally nonreactive with the components of the efinaconazole formulation and capable of maintaining the stability of the efinaconazole and excipients of the formulation over the desired storage period (e.g., for at least 12 months, at least 18 months, at least 24 months, at least 30 months, at least 36 months, or longer), preferably at ambient room temperature (e.g., at a temperature of about 20 to about 25° C., such as under controlled room temperature conditions of 20-25° C. (e.g., 22° C.)). The container can contain from 2 mL to 30 mL of efinaconazole formulation, such as about 3 mL, about 4 mL, about 5 mL, about 6 mL, about 8 mL, about 10 mL, about 15 mL, about 20 mL, or about 25 mL.

The container typically is in fluid communication with (is connected to or interconnected with in a manner that at least under some conditions permits flow) or can be made to be in communication with (i.e., connected to or interconnected with) an applicator that is used to apply the efinaconazole formulation to the target area of a patient. In some embodiments, an application device is provided separately. In some embodiments, part of an application means is integral to the container and part of it is separate (such as where the container includes a dropper or dropping means and is provided with a separate sponge or brush). The applicator can be any suitable device or component used to apply an efinaconazole formulation to the treatment areas (target areas or target treatment areas) of a patient. It will typically be made of materials that are non-reactive with the efinaconazole formulation. In general, non-reactive materials will not cause significant degradation of the efinaconazole, or any excipients of the formulation, and/or the binding, imbibition, absorption or adsorption of the efinaconazole, or any excipients of the formulation. The applicator will typically be configured to apply the drug product as desired to the target area according to the typical size and shape/configuration of onychomycosis treatment areas. Typically, approximately even distribution of the formulation to each nail and nail-associated area in a target area/treatment area is desired. As such, an applicator typically will be a device or component that is or comprises at least a member that is capable of spreading the formulation, such as a brush.

The applicator also often will be capable of dispensing a pharmaceutically acceptable dose when used appropriately. The dose does not necessarily have to be the same exact dose for each application, but typically the dosage is approximately equivalent and measured (or within an acceptable range) on each typical application. The applicator preferably allows the user to exert some control over the amount of material administered to each affected nail treatment area since toes and nails vary in size and degree of onychomycosis involvement. Commonly, the applicator is a component or device that is capable of being loaded with such a dose of the formulation by the user, either through absorption of the formulation (under conditions such that it can be released from the applicator typically when applied to the nail area for treatment) or by other means (e.g., by entrapment in a dense brush). Typically the volume of the formulation that is applied by the applicator is enough that one volume is able to evenly spread across an average sized toenail (with two doses typically being enough to cover a hallux).

When the applicator is loaded prior to administration, the loading can be performed by any suitable method. Loading can be, for example, performed by mechanical means, such as loading by pressure or by wicking that is associated with any kind of suitable means for exposing the wicking device or means to the efinaconazole formulation stored in the container (e.g., by the press of a button on the device by a user which opens a port that allows flow of the formulation to the wicking component). In certain embodiments, the applicator is loaded manually. For example, the container can be a pressure-reactive (squeezable) container and loading of the applicator can be accomplished by the user applying pressure to the device to sufficiently apply pressure to the formulation contained in the container and/or to open an orifice to permit flow of formulation from within the container to the applicator to load the applicator. It should be understood that even in embodiments where the applicator is not loaded, the use of such a manual method for administering the formulation to the applicator is provided (e.g., the applicator may not actually hold a dose but may be used to apply the dose to the target area after the dose is directly applied to the target area). In some embodiments, the applicator is loaded in part by gravity as the user changes the orientation of the container/applicator. In some embodiments, the loading of the applicator by wicking may entail touching the nail or treatment area to load the applicator.

Once the dose of formulation is delivered to the nail and nail-associated tissue the applicator is typically used to also spread the formulation over all of the target areas of the toe and associated tissue. Commonly, spreading is performed by user manipulation of the applicator (e.g., brushing with a brush applicator).

The container can be a single use container or a multiple user container. Single user containers can provide enough of the efinaconazole formulation for treatment of a particular target region, average target region, or maximum target region for a single daily application of multiple nails or can provide enough of the formulation for treatment of a single toenail.

The multiple use container typically will contain enough efinaconazole formulation for repeat use over a treatment period, usually at least about 4 weeks (30 days or about 1 month), at least about 8 weeks (or about 2 months), at least about 12 weeks (or 3 months) (e.g., at least 16 weeks or about 4 months, about 18 weeks, about 20 weeks, 24 weeks, 26 weeks, 28 weeks, 30 weeks, or about 32 weeks), but more commonly at least about 36 weeks (e.g., about 40 weeks or longer). In some embodiments, the container holds enough formulation for at least one 48-week treatment regimen of once a day application to some, most, or all of the toes of two feet. In some embodiments, the container holds enough efinaconazole formulation for multiple treatments. In some embodiments, the container contains about 2 mL to about 8 mL of the efinaconazole formulation (e.g., about 3 mL, about 4 mL, about 5 mL, about 6 mL, or about 7 mL).

A number of different applicators can be used to apply the formulation to the target area. Where the applicator is loaded with a dose prior to administration it typically will be the case that the applicator is a device capable of being loaded through wetting with the formulation in a manner that the applicator then holds the formulation until the user applies the applicator to the target area. In some embodiments, the applicator is a brush that is made of material that is suitable for holding a dose of efinaconazole formulation in such a manner. Applicators can be made of any suitable material or materials to administer and, if desired, hold a dosage of the efinaconazole formulation for administration. Brushes and other administrator means (applicators) can be made from, for example, plastic(s) such as low density polyethylene. Such materials can also be used to form a group of flexible plastic tubes or strips to act as an administrator. Alternatively, an applicator can be made from natural or synthetic fibers, or a fabric. Additional materials that can be useful for incorporation in an applicator include polyester and nylon materials. In some embodiments, the applicator is a pad that is made of a loadable material. In some embodiments, the applicator is a swab. Accordingly, the formulation may be rubbed, painted, dabbed, dripped, sprayed, wiped, spread, rolled (e.g., as with a roller ball applicator) or poured onto the affected nail and surrounding tissues. Alternatively, a formulation can be delivered by a soak or other sustained contact method.

Applicators can be for single use, a few uses, or frequent repeated use (over one treatment period or multiple treatment periods). Where applicators are designed for multiple uses, the device typically includes a cover (e.g., a cap) that can keep the applicator clean and not exposed to external environmental conditions, and can maintain the formulation potency during use and control evaporative loss of the formulation components. The cap can be of any suitable configuration and made of any suitable material, such as a plastic.

When the applicator is loaded with the efinaconazole formulation or otherwise contains the efinaconazole formulation, the applicator can hold any suitable volume. A volume might be sufficient for one treatment of a typical toe or a typical hallux or for a number of toenails or fingernails. Typically, the applicator is loaded with about 7 µl, such as about 7.5 µl to about 35 µl, or about 30 µl (e.g., about 8 µl or about 10 µl to about 25 µl or about 27 µl). In certain embodiments, the volume is in a range of about 15 to about 22.5 such as 16-20 µl.

By use of an applicator device according to various aspects of the invention provided herein a patient and/or healthcare worker administering the formulation does not contact the formulation with his or her hands in the performance of the method. It is advantageous to avoid hand contact with the efinaconazole formulation to avoid waste and inadvertent transfer to undesirable body areas such eyes or mouth. Methods of the invention can include providing instructions to the patient and/or healthcare provider in this respect.

In certain embodiments, the device comprises a container in the form of a plastic squeeze bottle and the applicator is a formulation-loadable brush, typically a flow-through brush applicator, which is contained by a cap that mates with (seals or at least blocks off) the container (e.g., through screw-on threading, snap ring or other means). The patient and/or health care provider is instructed to remove the cap, invert the bottle, and then squeeze to completely wet the brush. The user (patient and/or healthcare provider) then applies the wetted brush onto each nail in the target area to completely wet the nail and surrounding skin. In some embodiments, the patient is instructed to completely cover the nail, nail folds, nail bed, hyponychium, and as much of the undersurface of the nail plate. For a great (big) toenail (hallux), the user is instructed to make two applications or to load the applicator with approximately double the volume so that about twice the amount of formulation as is delivered to a non-hallux toe can be delivered to each treated great toe. Typically, the user is instructed to make a uniform application of the formulation (e.g., applying consistently and evenly to all areas of all nails treated). Usually such methods (and other methods of administering efinaconazole formulations provided herein) include a step of requiring the patient to wait for a suitable period of time (typically no more than 15 minutes, such as 10 minutes or less) before covering the treated area (e.g., with a sock, shoe, or other covering or other clothing).

In a more general sense (i.e., with or without the use of a device for delivering the efinaconazole formulation), the methods of the invention can be practiced with the inclusion of a requirement or step of approximately uniform distribution of an efinaconazole formulation to nails and nail-associated tissue. As administration is typically manually performed there will be some variation in the amount delivered to any area of the nail or surrounding skin. In some embodiments, the variation in the amount of efinaconazole administered to a given area of the nail is no more or less than 33% or no more or less than 25% in any other area or on average delivered to the nail (e.g., no more than 20%, 15%, or 10% or no more than 5% of a deviation from the greatest opposite amount (higher or lower) or average delivered to the corresponding area of the nail occurs). Also or alternatively the method can be characterized by a deviation of no more than 5%, 10%, 15%, 20%, 25%, 30%, or more of the administered formulation to a nail in the target area (or on average to the target area across all treated nails) per a measured unit area (e.g., square centimeter). This standard can be accomplished by uniform administration in combination with using a formulation that quickly penetrates the nail, examples of which are described elsewhere herein.

In a related aspect, the invention provides devices for storing and typically also administering efinaconazole formulations that are useful in the practice of methods provided herein. In some embodiments, the invention provides a device for treating fungal infections comprising (a) a container portion that securely holds a flowable pharmaceutical formulation of efinaconazole and that can maintain the formulation in a pharmaceutically acceptable state for extended periods of time at room temperature and (b) a loading portion that is capable of being loaded with a desired dose of the efinaconazole formulation when a user desires to apply a treatment, and (c) means for delivering the dose of the efinaconazole formulation by manual application evenly across the treatment area of a toe. The invention provides methods of controlled application in that approximately accurate amounts can delivered to with a degree of accuracy to a target area. In this respect, for example, no more than 15%, no more than 10%, nor more than 5%, or no more than 3% of the intended dosage of efinaconazole formulation is lost to non-target area applications. In some embodiments, the loading portion and delivery means are one and the same (e.g., where the device includes a loadable brush that is suitable for delivery of a dose of efinaconazole formulation to target area(s)). Such a device will typically include a cap or other cover (means for enclosure) for the delivery means and/or loading portion (e.g., a seal, a cover, or similar device known in the art of container manufacture). Commonly, the flowable formulation will be a liquid, but flowing gels, creams, ointments, lotions, and other flowing formulations also can be used. In some embodiments, the device is a squeezable plastic bottle, as described above, which is mated to and that can be in fluid communication with, upon application of manual pressure, a flow through applicator, such as a flow through brush applicator. In certain embodiments, the brush is capable of being loaded with an approximately set dose of efinaconazole formulation when wet.

The methods of the invention can be performed in a manner such that a complete cure rate (as described in the Experimental Methods section of this document) of at least 12% when tested in a suitable patient population (e.g., of at least about 50 patients, at least about 75 patients, at least about 100 patients, at least about 150 patients, at least about 250 patients, at least about 500 patients, at least about 750 patients, or at least about 1000 patients), such as at least 14%, or, more particularly, at least 15% is achieved in the population that receives treatment by the method. In some embodiments, methods of the invention are performed such that the outcome is a complete cure rate that is at least 5%, such as at least 7%, at least 8%, or at least 9% greater than the complete cure rate obtained with the vehicle alone when similarly tested in a suitable patient population.

By referring to performance or practice "in a manner" in this respect (i.e., to achieve such complete cure rates as described in the preceding paragraph), or in other respects where such a phrase is used herein in connection with methods that result in a particular outcome, it is to be understood that the aspect(s) of the invention being referred to or described require the selection/employment of appropriate factors/variables in terms of, e.g., formulation, dosage, duration of treatment, etc., to achieve the specified outcome. Employment of particular and preferred methods provided herein (e.g., treatment with the formulation known as IDP-108), in a non-occluded fashion (e.g., without occluding, blocking or covering the nail with, for example, adhesive tape, bandage, dressing, sealant, etc.), including 10% efinaconazole (w/w), for a 48-week treatment period with a 4 following week evaluation period (non-treatment period after which evaluation of efficacy was/is made), with no debridement or removal of the drug required, delivered from a device including a flow through brush applicator and relatively uniform spreading throughout each nail treated in a target area by complete covering of the nail, nail folds, nail bed, hyponychium, and as much of the undersurface of the nail plate) will provide such results, but the inventors also expect that reasonable variations from such methods can be made by those of ordinary skill in the art using only routine experimentation with the achievement of similar results given the guidance provided herein.

In certain embodiments, methods as described herein are performed such that the method also or alternatively obtains a mycological cure rate (as described in the Experimental Methods section of this document) of at least about 40%, such as at least about 45%, or at least about 50% when tested in a suitable patient population (e.g., of at least about 50 patients, at least about 75 patients, at least about 100 patients, at least about 150 patients, at least about 250 patients, at least about 500 patients, at least about 750 patients, or at least about 1000 patients). In some embodiments, the method is performed so as to provide a mycological cure rate that is at least 25%, such as at least 30%, or at least 35% better than vehicle when tested in a similarly suitable patient population.

In some embodiments, methods of the invention also or alternatively result in a complete or almost complete cure rate (as described in the Experimental Methods section of this document) of at least about 15%, such as at least about 20%, such as about 25% or higher when tested in a suitable patient population (e.g., of at least about 50 patients, at least about 75 patients, at least about 100 patients, at least about 150 patients, at least about 250 patients, at least about 500 patients, at least about 750 patients, or at least about 1000 patients). In some embodiments, treatment methods are performed such that the complete or almost complete cure rate that is at least about 10%, such as at least 12%, or at least 15% better than that which is achieved using corresponding vehicle in the patient population or a similarly suitable patient population.

In some embodiments, the methods also or alternatively result in a clinical efficacy rate (as described in the Experimental Methods section of this document) of at least about 20%, such as at least about 25%, or at least about 30% when tested in a suitable patient population (e.g., of at least about 50 patients, at least about 75 patients, at least about 100 patients, at least about 150 patients, at least about 250 patients, at least about 500 patients, at least about 750 patients, or at least about 1000 patients). In some embodiments, the clinical efficacy rate when tested in a suitable patient population is better by at least about 12% (such as at least about 15%, or at least about 20%) as compared to the result obtained with a corresponding vehicle alone when studied in an appropriate patient population.

In some embodiments, treatment methods using the techniques provided herein are performed such that the rate of application site dermatitis (such as local irritation) in a population of patients (e.g., of at least about 50 patients, at least about 75 patients, at least about 100 patients, at least about 150 patients, at least about 250 patients, at least about 500 patients, at least about 750 patients, or at least about 1000 patients) is about 4% or less or about 3% or less, such as about 2.5% or less and/or is less than about 3% such as less than about 2% greater than the application site dermatitis rate seen when administering a corresponding vehicle to the patient population or a different but also suitable patient population.

In some embodiments, the methods also or alternatively are performed such that the rate of application site vesicle formulation (i.e., blistering in the skin in and around the treatment area) also or alternatively is less than about 3%, such as less than about 2%, or only about 1.5% in a patient population (e.g., of at least about 50 patients, at least about 75 patients, at least about 100 patients, at least about 150 patients, at least about 250 patients, at least about 500 patients, at least about 750 patients, or at least about 1000 patients).

In addition to the treatment of onychomycosis, the methods provided herein can be used for other suitable purposes including the inhibition of fungal lanosterol 14α-demethylase and/or ergosterol biosynthesis. For example, the methods can be applied to inhibit the growth of and/or to eradicate a microorganism, such as a dermatophyte, for example a dermatophyte of the *Tricophyton, Microsporum*, and *Epidermophyton* species and/or a yeast (e.g., a yeast of the *Malassezia* species or *Candida* species). In certain embodiments, the methods can be employed to inhibit and/or eradicate microorganisms selected from *Trichophyton mentagrophytes, Trichophyton rubrum, Candida albicans, Trichophyton tonsurans, Trichophyton verrucosum, Trichophyton schoenleinii, Epidermophyton floccosum, Scopulariopsis brevicaulis, Acremonium* spp., *Fusarium* spp., *Candida parapsilosis, Candida krusei, Candida tropicalis*, and *Microsporum canis*.

EXAMPLES

The following examples further illustrate the invention but, of course, should not be construed as in any way limiting its scope.

Preclinical Studies

Efinaconazole drug resistance development was studied in vitro against *T. mentagrophytes, T. rubrum* and *C. albicans*. Serial passage of fungal cultures in the presence of sub-growth inhibitory concentrations of efinaconazole increased the MIC by up to 4-fold, suggesting low resistance development potential. The clinical significance of these in vitro results is unknown.

In a 2-year dermal carcinogenicity study in mice, IDP-108 showed no evidence of carcinogenicity at efinaconazole doses of up to 140 mg/kg/day (equivalent to approximately 16 and 248 times the clinical maximum use dose based on mg/m2 and AUC, respectively).

Efinaconazole was not mutagenic in a bacterial reverse mutation assay and was not clastogenic in mouse micronucleus and CHL cell chromosomal aberration tests. In a fertility and early embryonic development study, subcutaneous efinaconazole administration to rats at doses up to 25 mg/kg/day had no effect on fertility in males or females. Efinaconazole delayed the estrous cycle in females at 25 mg/kg/day but did not have effects at 5 mg/kg/day (equivalent to 58 times the clinical maximal use dose based on AUC).

Nail Penetration Study

Nail penetration studies were performed using efinaconazole formulations and a ciclopirox formulation.

For the nail penetration studies permeation cells were assembled according to standard operating procedure applying the following variables:

A. Cell: Teflon one-chamber diffusion cell.

B. Receptor Fluid: A small cotton ball wetted with 0.1 ml normal saline.

C. Incubation Temperature and Humidity: Room temperature (20-30° C.), 30-45% RH.

D. Surface Area: One (1) cm in diameter, 0.785 $cm^2$.

E. Formulation: 5% w/w IDP-108 Formulations (see below)

F. Dose Volume and Frequency: Ten (10) μl/dose, once (9-10 AM).

G. Dose Contact Time and Surface Washing:

Each dose contact time was 24 hrs. Surface washing is with ethanol, soap and water at the next day morning 10 minutes prior to next dose.

H. Sampling Sources:
1. Surface washes, inner washes.
2. Cotton ball (supporting bed) 3. Nail content

STUDY DESIGN

A. Treatments

| Study Day | Groups Group ID (A, B, C, or D) | | | |
|---|---|---|---|---|
| | Surface Washing | Dose | Changing Cotton Ball | Nail Sampling |
| 1 | | X | | |
| 2 | X | X | | |
| 3 | X | X | Z | |
| 4 | X | X | | |
| 5 | X | X | Z | |
| 6 | X | X | | |
| 7 | X | X | Z | |
| 8 | X | X | | |
| 9 | X | X | Z | |
| 10 | X | X | | |
| 11 | X | X | Z | |
| 12 | X | X | | |
| 13 | X | X | Z | |
| 14 | X | X | | |
| 15 | X | | Z | Y |

X=once per day (9~10 AM).

Y=nail samples.

Z=remove and/or replace cotton ball samples.

Sample size (number): Five (5) per group.

B. Dosing Procedure

Chemicals in formulations dosed at 10 μl/$cm^2$ initially and thereafter once daily (9-10 am) for 14 days (total of 14 multiple dosing).

C. Surface Washing and Final Cell Washing

1. Ten minutes prior to the morning application (excluding the first application), the dosed area of the nail plate was washed with cotton tips in a cycle as follows:

a tip wetted with ethanol, then a tip wetted with ethanol, then a tip wetted with 50% skin cleansing liquid IVORY soap, then a tip wetted with distilled water, then a tip wetted with distilled water, then a final dry tip.

All tips were collected into a single vial.

2. Test materials were applied in quantities identified in "Experimental Design" above.

3. When the whole incubation period finished, after removal of the nail plate and nail bed, the cell was washed as the same as the surface washing procedure.

D. Cotton Ball Nail Supporting Bed

The cotton ball was changed and replaced every 48 hours after first dose application until the end of the dosing/incubation period. The processes were conducted at the same time of surface washing. All cotton ball samples were individually collected and radioactivity counted.

Study Formulations

|  | Formulation ID | | | |
|---|---|---|---|---|
|  | 0001-2313-078 | 0001-2313-080 | 0001-2313-082 (C) | 0001-2313-107 |
| Batch Number | 2313-022 | 2313-024 | 2313-026 | 2313-053 |
| efinaconazole | 5.00% | 5.00% | 5.00% | 5.00% |
| ethanol | 19.35% | 20.00% | 59.998% | — |
| triacetin | 15.00% | — | — | — |
| glycerin | 35.00% | 24.998% | — | — |
| 1,3-butylene glycol | 25.00% | — | — | — |
| carbomer 980 | 0.50% | — | — | — |
| diisopropanolamine | 0.10% | — | — | — |
| tocopherol | 0.05% | 0.002% | 0.002% | 0.05% |
| propylene glycol | — | 50.00% | — | — |
| cyclomethicone | — | — | 13.00% | — |
| diisopropyl adipate | — | — | 12.00% | 8.20% |
| myristyl lactate | — | — | 10.00% | — |
| isopropyl myristate | — | — | — | 5.48% |
| White Petrolatum | — | — | — | 51.27% |
| Urea | — | — | — | 30.00% |
| Total | 100% | 100% | 100% | 100% |

Figure 2:
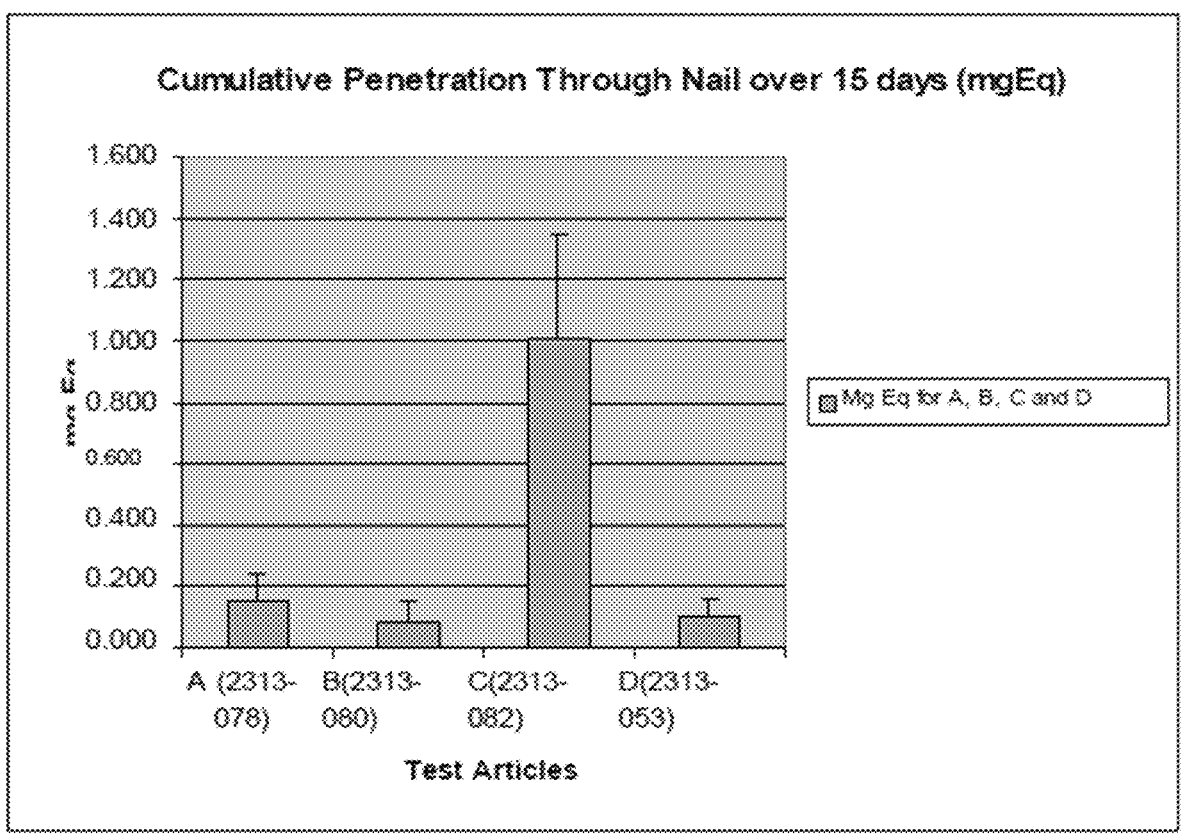
FIG. 2 shows the cumulative penetration of efinaconazole over 15 days through the nail, expressed in mg Eq, exhibited in preclinical studies.
Figure 3:
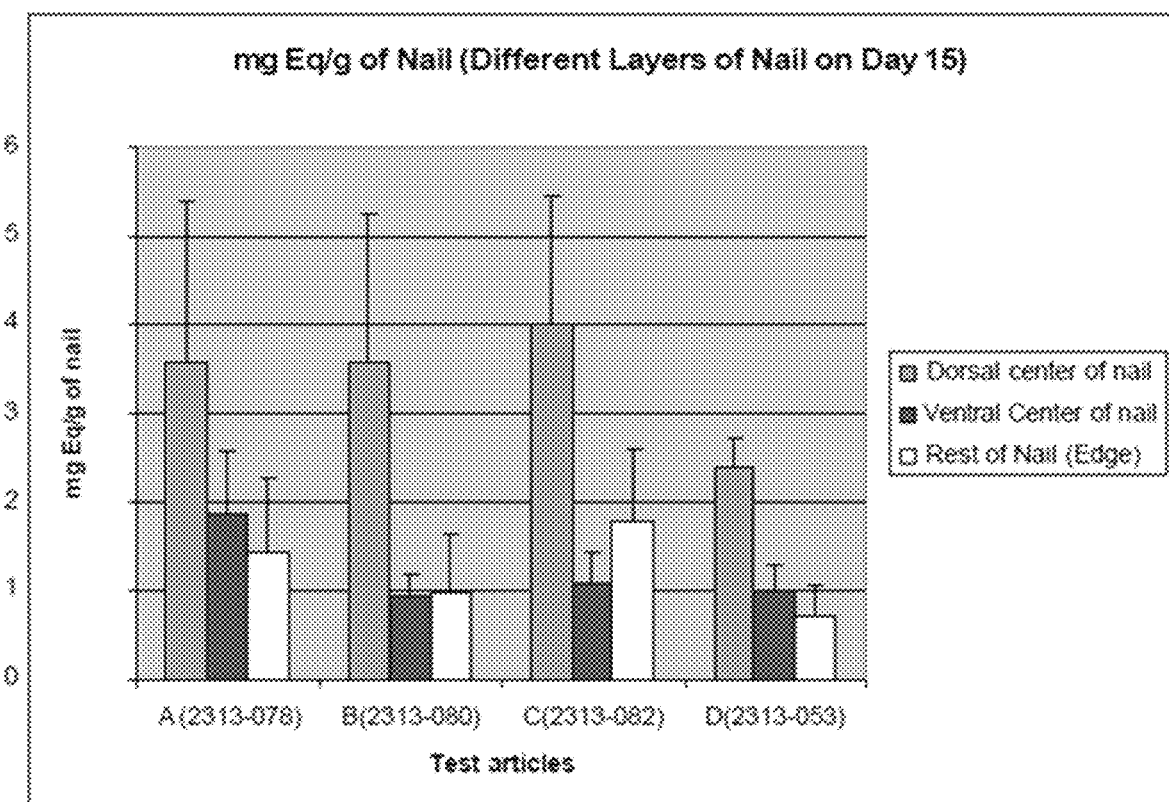
FIG. 3 shows the amounts of efinaconazole in different layers of nail on Day 15.

Certain results of the penetration studies are shown in FIGS. 1, 2, and 3.

Figure 4A:
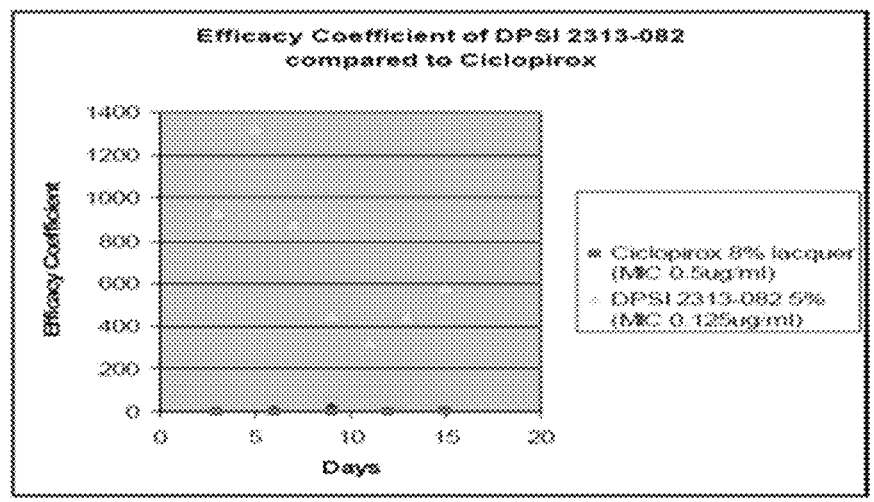
FIG. 4A shows the comparison of efficacy coefficient (flux/MIC) for an efinaconazole formulation of the invention (DPSI 2313-02) and ciclopirox 8% lacquer over 15 days. Flux=µg eq/cm$^2$/day; MIC=µ/mL.
Figure 4B:
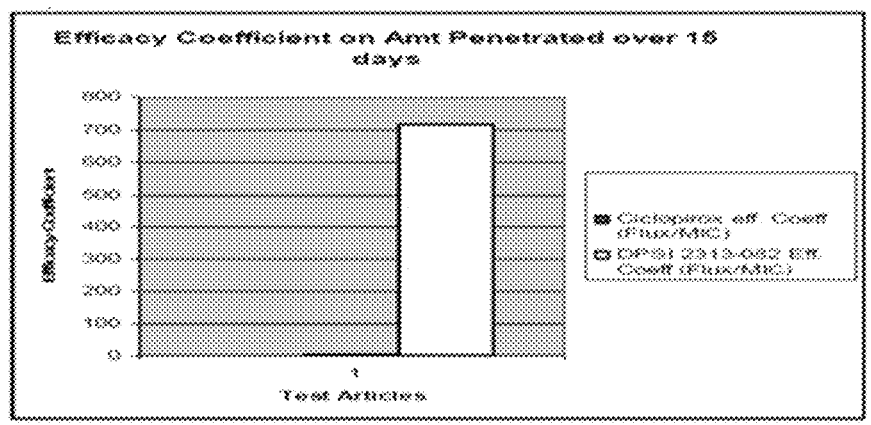
FIG. 4B shows the comparison of efficacy coefficient (flux/MIC) for an efinaconazole formulation of the invention (DPSI 2313-02) and ciclopirox 8% lacquer based on cumulative amount penetrated over 15 days. Flux=µg eq/cm$^2$/day; MIC=µ/mL.

The results of the comparative studies between efinaconazole 5% formulation C (DPSI 2313-082) (relating penetration to MIC data) and a ciclopirox lacquer formulation are shown in FIG. 4. As demonstrated from this data, efinaconazole formulations provide a surprisingly high efficacy coefficient as compared to the standard topical therapy for treatment of onychomycosis. In some embodiments, the invention provides methods that result in an efficacy coefficient similar to or better than those demonstrated in this example (e.g., an efficacy coefficient of at least about 200 μg eq/cm$^2$/day)/(μg/ml) [MIC], such as at least about 300 500 μg eq/cm$^2$/day)/(μg/ml), or even, especially on average, 400 or 500 μg eq/cm$^2$/day)/(μg/ml)) (e.g., an average of about 700 μg eq/cm$^2$/day)/(μg/ml)).

Clinical and Safety Studies

Pilot Clinical Efficacy Study

A multicenter, randomized, double-blind, vehicle-controlled phase 2 study of a 10% efinaconazole formulation, IDP-108, in mild to moderate toenail Distal lateral subungual onychomycosis (DLSO) (n=135) was conducted. Subjects randomized (2:2:2:1 ratio) to receive IDP-108 (with or without semi-occlusion)(n=36 and n=39, respectively), an efinaconazole 5% solution (n=38), or vehicle (n=22), once daily for 36 weeks, with one 4-week post treatment follow-up (week 40). Efficacy assessments included complete cure, mycologic cure, clinical efficacy, and other assessments of overall treatment effectiveness. No efficacy variables were designated as primary.

In addition to 10% w/w efinaconazole, IDP-108 contains 13% cyclomethicone, 12% diisopropyl adipate, 10% C12-15 alkyl lactate, 1% purified water, and small amounts of citric acid, anhydrous, edetate disodium, and BHT, as described in the '569 provisional, in addition to small amounts of vitamin E (0.05%), with the remainder of the formulation being made up of alcohol (alcohol/dehydrated alcohol USP).

At follow-up, complete cure was numerically higher in all active groups (16%-26%) compared with vehicle (9%). Mycologic cure rates with IDP-108 10% semi-occlusion, IDP-108 10%, and efinaconazole 5% were 83%, 87%, and 87%, respectively. Efinaconazole 10% (with or without semi-occlusion) demonstrated significantly greater clinical efficacy and treatment effectiveness when compared with vehicle (P=0.0088 and 0.0064; 0.0056 and 0.0085, respectively, for both efinaconazole 10% groups). Adverse events were generally similar among treatment groups and mild. Local-site reactions were restricted to few subjects and did not differ meaningfully from those produced by vehicle. Methods of treatment were generally similar to those described above in connection with Study 1 and/or Study 2. Subjects in the semiocclusion treatment arm also were provided with semi-occlusive dressings and were instructed to apply the dressings overnight to the target toenail at least 10 minutes after the study drug had been applied.

The mean area of the target toenail was 40.3%, and the mean number of affected non-target toenails (including great toenails and other affected toenails) was 4.9. 117 (86.7%) of subjects completed the study. The most frequent reasons for study discontinuation were being lost to follow-up (n=8, 5.9%), subject request (n=3, 2.2%), and AEs (n=3, 2.2%). The proportion of subjects with mycologic cure and either an affected target toenail area of 0% or >3 mm proximal nail growth from baseline in the unaffected target toenail at follow-up was 61%, 64%, 55%, and 23%, respectively (FIG. 5; P=0.0041, 0.0030, and 0.0158 vs. vehicle). All analyses were performed using SAS software (version 9.1.3).

Overall, efinaconazole 10% solution (with or without semi-occlusion) demonstrated significantly greater clinical efficacy and significantly greater healthy target toenail growth with no additional benefits of semi-occlusion. This final surprising result suggests that 10% efinaconazole applied once a day can be an optimal concentration in the context of a topical formulation for onychomycosis treatment.

Figure 5:
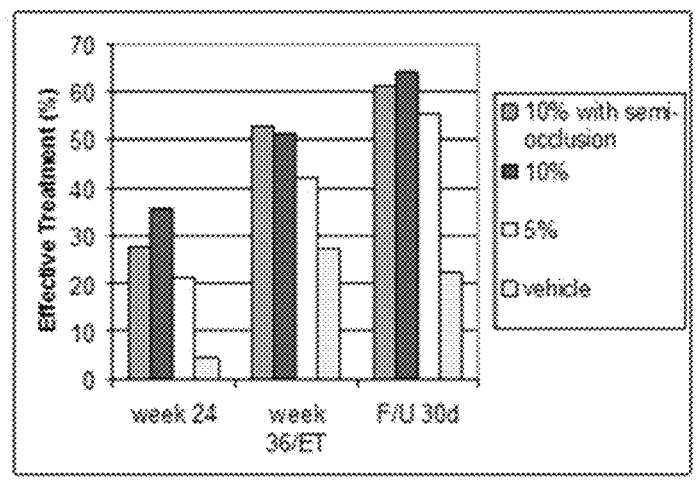
FIG. 5 shows the levels of effective treatment—mycological cure and either clear nail (0% affected area) or ≥3 mm healthy unaffected nail growth—resulting from treatment of onychomycosis patients with efinaconazole formulations.

Data from this study is illustrated in FIG. 5 which shows that treatment with 10% efinaconazole formulation (IDP-108) resulted in a surprisingly high treatment success (complete cure) rate as compared to 5% efinaconazole and 10% occluded efinaconazole formulation treatments particularly after the end of treatment (30 days). Unexpectedly, administration of efinaconazole 10% solution without semi-occlusion resulted in increased efficacy at 24 weeks and at follow up, as compared to administration of efinaconazole 10% solution with semi-occlusion. Higher efficacy with semi-occlusion would have been expected, given that occlusion tends to increase drug flux into target tissues. Methods that do not require occlusion, in particular, can provide a number of advantages including reduced systemic exposure to active agents as well as reinforced patient compliance.

Efinaconazole 5% solution was also effective as compared to vehicle. As such, various aspects of the invention can be performed with a 5% formulation (or formulation with an approximately similar amount of efinaconazole, e.g., 3.5-7.5%, such as 4-6%), and a greater than 10% efinaconazole formulation (e.g., 11%, 12%, 13%, 14%, or 15% efinaconazole w/w) given the fact that 10% semi-occlusion also resulted in significantly better results than vehicle, but with about 10% efinaconazole (e.g., about 8-12%, such as about 8.5-11.5%, such as 9-11% or 9.5-10.5%) being generally preferred for use in the methods and devices, products, and formulations of the invention provided herein.

Large Scale Clinical Studies

The safety and efficacy of once daily use of a 10% efinaconazole formulation (IDP-108) for the treatment of onychomycosis of the toenail were assessed in two identical 52-week prospective, multi-center, randomized, blinded studies in adult patients 18 years and older (18 to 70 years of age) with 20% to 50% clinical involvement of the area of the target big toenail, without dermatophytomas or lunula (matrix) involvement. Patients were not excluded for concomitant *Candida* infection.

The study included men and women of any race and had clinical diagnoses of distal lateral subungual onychomycosis affecting at least one great toenail (hallux). Subjects must have had mild to moderate onychomycosis, defined as clinical involvement of 20% to 50% of the area of the target great toenail, without dermatophytomas or lunula (matrix) involvement. The target great toenail must have had an uninfected length greater than or equal to 3 mm, a thickness no greater than 3 mm, evidence of toenail growth, a positive microscopic examination with KOH for the hyphae associated with dermatophytes, and a positive dermatophyte culture or mixed dermatophyte/*Candida* culture within 42 days prior to the Baseline Visit (start of treatment).

The studies compared 48-weeks of treatment with IDP-108 to a corresponding vehicle solution.

One application of IDP-108 (10% efinaconazole solution) was applied daily at bedtime to all affected toenails (the treatment area), as determined by the investigator. For each treated toenail, the study drug solution was applied such that the nail folds, nail bed, hyponychium, and top and undersurface of the nail plate (where applicable) were completely covered.

All statistical processing was performed using SAS software (SAS Institute, Inc.; Cary, N.C.). Two-sided hypothesis testing was conducted for all analyses and statistical inferences were drawn at an alpha level of 0.05. Missing efficacy data were imputed using the last observation carried forward (LOCF) method; no imputations for missing safety data were performed.

All adverse events (AEs) that occurred during the study were recorded and classified using the Medical Dictionary for Regulatory Activities (version 12.1). Treatment-emergent adverse events (TEAEs) (i.e., events that began after the first application of study drug) that occurred during the study were summarized by treatment group, the number of subjects reporting TEAEs, system organ class, preferred term, severity, relationship to study drug, and seriousness. Serious adverse events (SAEs) were also summarized separately. A Fisher's exact test was used to compare the incidences of TEAEs and treatment-related TEAEs by treatment group for events occurring with frequencies of 1% or more.

The primary efficacy endpoint was the "Complete Cure" rate at Week 52 (4-weeks after completion of therapy), defined as 0% involvement of the target nail (nail is totally clear of the signs of onychomycosis) in addition to "Mycologic Cure", defined as both negative fungal culture and negative KOH test for fungal elements.

Subjects in the ITT analysis set in the first study (Study 1 or Study One), 656 (75.4%) were randomized to treatment with IDP-108 and 214 (24.6%) were randomized to treatment with Vehicle. The mean (SD) area of the affected toenail (as a percent) was 36.7% (10.4) and the mean (SD) number of affected non-target toenails was 2.8 (1.7). Subjects in the IDP-108 and Vehicle groups administered a similar mean number of study drug applications and used a similar mean amount of study drug. Overall, 90.8% of the subjects in the IDP-108 group and 92.2% of the subjects in the Vehicle (formulation only) group were compliant with study drug administration.

Tables 1 and 2 below summarize the efficacy results for Studies 1 and 2.

TABLE 1

Primary Efficacy Endpoint (Complete Cure) ITT (intent to treat) Subjects

| | Study 1 | | Study 2 | |
|---|---|---|---|---|
| | Active N = 656 | Vehicle N = 214 | Active N = 580 | Vehicle N = 201 |
| Complete Cure | 117 17.8% | 7 3.3% | 88 15.2% | 11 5.5% |

Study 1 consisted of 15 visits, including Screening (up to Day—42), Baseline (Day 0), 12 treatment visits (Weeks 4, 8, 12, 16, 20, 24, 28, 32, 36, 40, 44, and 48 [or Early Termination]), and one four-week post-treatment follow-up visit (Week 52). Efficacy and safety assessments were performed throughout the study. Specifically in regard to efficacy, the growth of the target toenail was measured at all post-baseline visits. Clinical assessments of the target and non-target toenails were conducted at Baseline, and were repeated at 12-week intervals post-baseline (i.e., Weeks 12, 24, 36, and 48) and prior to exit (Week 52). Clippings for samples of the target toenail were collected at Screening, Weeks 12, 24, 36, 48, and 52 week follow-up for potassium hydroxide (KOH) examination and mycological culture by the central mycology laboratory. Finally, subjects whose native language was English completed the OnyCOE-t™ quality of life questionnaire at Baseline, and at Weeks 24 and 52. Adverse events (AEs) and assessments of localized skin reactions were recorded at the Baseline Visit, as well as at every post-baseline study visit through either Week 48 (skin reactions) or Week 52 (AEs).

In addition, the following endpoints in Table 2 were also evaluated and include "Mycologic Cure" (defined as a negative fungal culture and a negative KOH examination of the target toenail), "Complete or Almost Complete Cure" (defined as an area less than or equal to 5% of the affected target toenail in addition to a negative fungal culture and a negative KOH examination of the target toenail sample), "Clinical Efficacy" (defined as an affected target toenail area of less than 10%) and "Unaffected New Nail Growth" (defined as the change from baseline in the healthy [unaffected] target toenail measurement for the target toenail).

TABLE 2

Secondary Efficacy Results at Week 52 in Studies 1 and 2 - ITT Subjects

| | Studies 1 and 2 | |
|---|---|---|
| | Active N = 1236 | Vehicle N = 415 |
| Mycologic Cure | 672 (54.4%) | 70 (16.9%) |
| Complete or Almost Complete Cure | 309 (25.0%) | 30 (7.2%) |
| Clinical Efficacy | 414 (33.5%) | 49 (11.8%) |
| Unaffected new Nail Growth (mm) | Mean | |
| | 4.3 | 1.1 |

The data described below reflect exposure to IDP-108 in 1227 patients from two clinical studies (Studies 1 and 2), of which 1161 have been exposed for 6 months and 780 exposed for 48 weeks. Related adverse events reported within the 48 weeks of treatment and in at least 1% of subjects treated with IDP-108 and those reported in subjects treated with the vehicle are presented in Table 3. IDP-108 may cause local reactions such as irritation comprising erythema, itching, burning, and/or stinging in the surrounding skin. In general, these adverse events were mild, transient, and did not lead to discontinuation from study participation. In addition IDP-108 may cause other skin reactions such as blisters (vesicles) in the surrounding skin treated or contacted with the formulation.

TABLE 3

Drug-Related Adverse Events Reported by at Least 1% of Patients Treated for up to 48 Weeks

| Adverse Event, n (%) | Active N = 1227 | Vehicle N = 413 |
|---|---|---|
| Application site dermatitis | 26 (2.1%) | 1 (0.2%) |
| Application site vesicles | 18 (1.5%) | 0 (0.0%) |

Figure 6A:
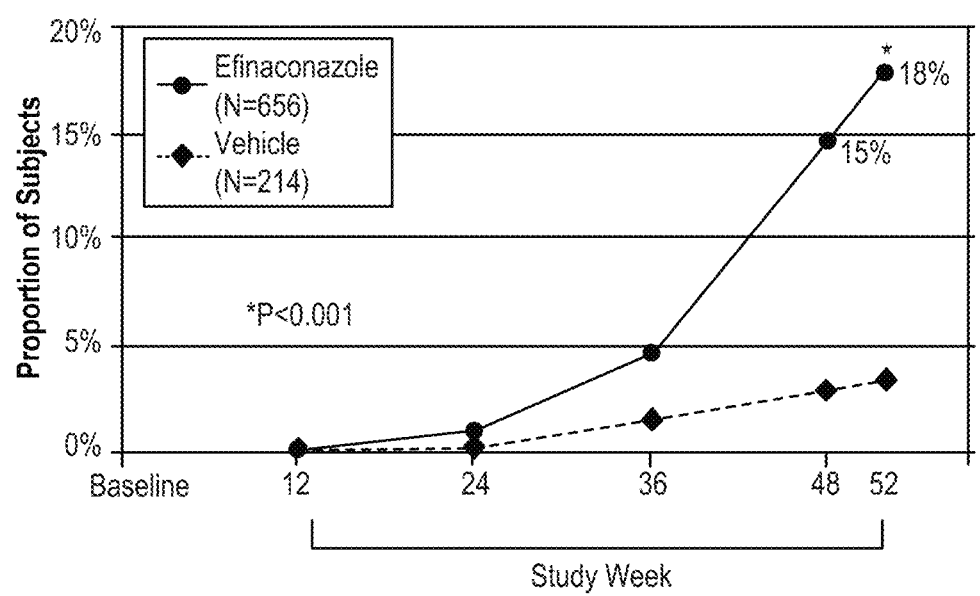
FIG. 6A and FIG. 6B show the proportion of onychomycosis patients demonstrating complete cure after treatment with 10% efinaconazole formulations according to the methods of the invention.
Figure 6B:
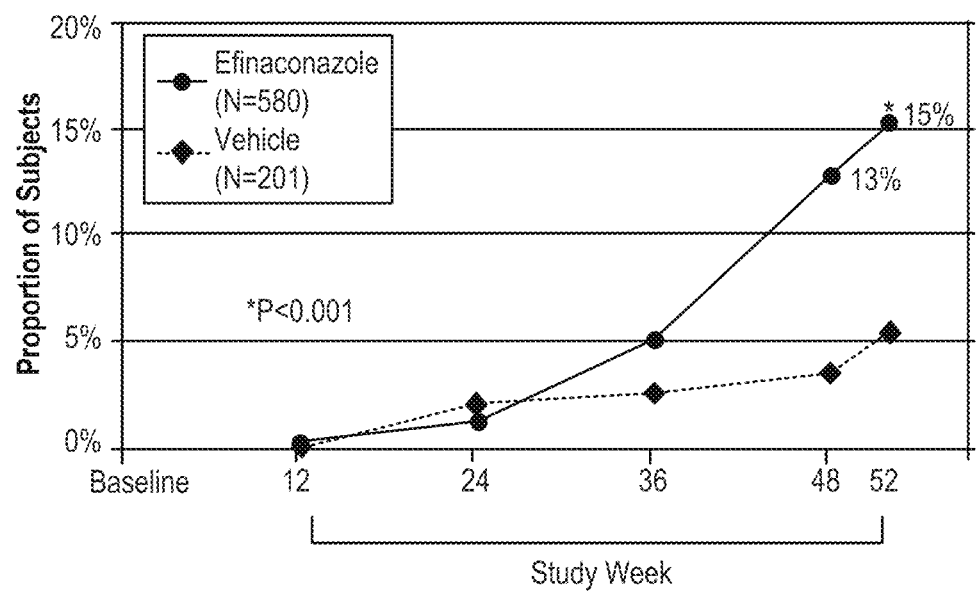

In Study 1, overall, 17.8% of the subjects in the IDP-108 group had a Complete Cure at Week 52 compared with 3.3% of the subjects in the Vehicle group (p<0.001). With respect the second efficacy measures, the Clinical Efficacy rate at Week 52 was 35.7% in the IDP-108 group compared with 11.7% in the Vehicle group (p<0.001). 55.2% of the IDP-108 subjects had a Mycologic Cure at Week 52 compared with 16.8% of the Vehicle subjects (p<0.001). The mean unaffected new toenail growth at Week 52 was 5.0 mm in the IDP-108 group compared with 1.6 mm in the Vehicle group (p<0.001). Finally, 26.4% of the IDP-108 subjects had a Complete or Almost Complete Cure at Week 52 compared with 7.0% of the Vehicle subjects (p<0.001). At Week 52 (after a four week post treatment assessment), greater efficacy was observed for IDP-108 relative to Vehicle in regard to the mean [SD] change from baseline in the number of affected non-target toenails (0.8 [1.5] versus −0.1 [1.2], respectively); the percentage of subjects with clear nails (21.3% versus 5.6%, respectively); the percentage of subjects with almost clear nails (35.1% versus 10.7%, respectively); and the percentage of subjects who achieved Clinical Efficacy (44.8% versus 16.8%, respectively). The mean [SD] target toenail growth was similar in the IDP-108 and Vehicle groups at Week 52 (22.2 [6.4] mm and 23.2 [7.6] mm, respectively). The complete cure endpoints over time are shown in FIG. 6A and FIG. 6B.

The results of the OnyCOE-t in Study 1 showed improvements in quality of life among subjects who used IDP-108 for 24 weeks and 52 weeks. The improvements observed among subjects in the IDP-108 group were maintained throughout the 52-week study duration and were consistently greater than the improvements observed among subjects in the Vehicle group. This demonstrates that in another aspect, the invention provides a method for improving the quality of life of an onychomycosis patient through the practice of methods described herein (e.g., administration of IDP-108 for 48 weeks, once daily, typically by use of a brush applicator for uniform distribution of the drug without the need for debridement).

The percentage of subjects in each treatment group who experienced 1 or more AEs was generally similar, as was the percentage of subjects in each treatment group who experienced 1 or more. There were 36 SAEs (2.4% of the total reported events). None of the SAEs were considered by the investigators to be treatment-related. The AEs reported during the study were generally mild or moderate in severity (96.1% of the events), not related to the study drug (93.5% of the events), and resolved with or without sequelae (84.6% of the events). Overall, 21 subjects (3.2%) in the IDP-108 group compared with 1 subject (0.5%) in the Vehicle group discontinued the study because of one or more AEs. The most common AEs that led to study discontinuation were treatment-related and were associated with the application site. The most commonly reported treatment-related events (i.e., AEs experienced by 1% or more of the subjects in either study drug group regardless of seriousness or severity) included application site dermatitis and application site vesicles; these events were experienced only by subjects in the IDP-108 group and occurred with frequencies of 3.4% and 1.8%, respectively. No other treatment-related events occurred at a frequency of 1% or more. The analysis of localized skin reaction scores indicated that once daily application of IDP-108 for 48 weeks generally did not result in redness, swelling, burning, itching, or vesiculation and did not produce localized skin reactions that differed meaningfully from those produced by the Vehicle. No mean changes in clinical laboratory parameters over time, no shifts in the percentages of subjects who had normal values at Screening and abnormal values at subsequent visits, and no individually significant laboratory results reported as AEs were indicative of a safety signal or indicated a clinically meaningful difference between IDP-108 and Vehicle. No clinically meaningful changes from baseline were observed in vital sign measurements or ECG results for either treatment group.

The conclusion from Study 1 was that IDP-108 was superior to Vehicle in both the primary and secondary efficacy analyses and showed consistently greater efficacy relative to Vehicle in each of the descriptive, supportive efficacy assessments. Based on these results, IDP-108 is effective for the treatment of distal lateral subungual onychomycosis when applied once daily for 48 weeks. Additionally, IDP-108 was generally safe and well tolerated among adult subjects with distal lateral subungual onychomycosis.

Overview of Safety Studies

Overall, safety of topical formulations of efinaconazole, such as IDP-108, was evaluated through 7 clinical studies involving 2114 subjects, 1663 (78.7%) of whom were exposed to various concentrations/formulations of IDP-108 (original formulation or the to-be-marketed formulation with efinaconazole concentrations of 1%, 5%, or 10%), and 1495 (70.7%) of whom were exposed specifically to the IDP-108 10% topical efinaconazole formulation. IDP-108 was well tolerated in all formulations and at each concentration evaluated in the Phase 1 studies.

Pharmacodynamic Studies/Evaluations

Systemic absorption of efinaconazole in 18 healthy patients with severe onychomycosis was determined after application of IDP-108 (10% efinaconazole) once daily for 28 days to patients' 10 toenails and adjacent skin. Specifically, two single-center, open-label studies in healthy volunteers and severe onychomycosis patients.

In healthy patients, efinaconazole 10% solution (IDP-108) was applied topically to all 10 toenails (0.42 mL total daily dose volume) administered as single and then 7 daily doses to 10 healthy volunteers, and once daily for 28 days to 18 severe onychomycosis patients. The efinaconazole 10% solution (0.42 mL/subject) was applied topically in the morning, unoccluded (i.e., without occluding, blocking or covering the nail with, for example, adhesive tape, bandage, dressing, sealant, etc.), by a trained nurse or study technician to all 10 toenails as a single dose (day 1), and seven consecutive daily doses (day 4 through day 10). A volume of 90 μL was applied on each great toenail and 30 μL on each of the remaining 8 toenails. There were no study drug applications on days 2 and 3.

Blood samples were collected at pre-dose, and 1, 2, 4, 6, 8, 10, 12, 16, 24, 28, 32, 36, 48, and 72 hours after dosing on days 1 and 10; and at pre-dose on days 6 and 8. Blood was processed to plasma and stored frozen until analysis.

A separate single-center, open-label study to evaluate safety and PK of efinaconazole and its H3 metabolite in 20 patients with severe toenail onychomycosis also was conducted. The study enrolled men and women 18-70 years of age who had clinical diagnoses of stable or exacerbating severe DLSO affecting ≥80% of the area of both great toenails. The great toenails had evidence of toenail growth, and at least four toenails other than the great toenails were also affected by onychomycosis. A positive microscopic examination with potassium hydroxide (KOH) for the hyphae associated with dermatophytes was obtained for at least one great toenail at the screening visit.

Efinaconazole 10% solution (0.42 mL/subject) was applied topically, unoccluded, once daily in the morning for 28 days to all 10 toenails by a trained nurse or study technician, including to the toenail folds, toenail bed, hyponychium, and approximately 0.5 cm of skin around the toenail in all directions to ensure they were completely covered.

Blood samples were collected at predose and at 1, 2, 4, 6, 8, 10, 12, 16, and 24 hours postdose on days 1, 14, and 28. Blood was processed to plasma and stored frozen until analysis.

Plasma concentrations of efinaconazole and its major metabolite H3 were determined by LC-MS-MS at multiple timepoints. Plasma concentrations of efinaconazole and H3 were determined using a validated LC-MS-MS method. The assay used 0.1 mL of plasma and had a lower limit of quantitation of 0.1 ng/mL for both analytes. The concentration of efinaconazole in plasma was determined at multiple time points over the course of 24-hour periods on days 1, 14, and 28. Plasma concentrations below the lower limit were set to zero for PK analyses. Pharmacokinetic parameters were calculated from individual plasma concentrations, whenever possible, using noncompartmental analysis in WinNonlin (Pharsight, Sunnyvale, Calif., USA), and included $C_{max}$ (observed peak drug concentration), $T_{max}$ (time at which $C_{max}$ occurs), $C_{min}$ (observed minimum drug concentration), $t_{1/2}$ (apparent half-life), and AUC (area under the concentration-time curve).

Both parent drug and metabolite accumulated following repeat dosing, and reached steady state in plasma by 14 days. Efinaconazole was well tolerated in both studies; no drug-related adverse events were reported. Efinaconazole mean plasma $C_{max}$ on Day 28 was 0.67 ng/mL. The mean plasma concentration versus time profile was generally flat over the course of treatment. In a separate study of healthy volunteers, the plasma half-life of IDP-108 (10% efinaconazole) in a single application when applied to all 10 toenails was 29.9 hours.

Both efinaconazole and H3 were detected in plasma after single and repeated application in healthy volunteers. The plasma concentrations-time profiles were flat on both days 1 and 10, showing slow drug absorption without an apparent elimination phase, characteristic of flip-flop kinetics. The plasma levels of H3 were consistently higher than those observed for efinaconazole. Additional results of the PK study in healthy volunteers are summarized in Table 4.

TABLE 4

Pharmacokinetic Parameters of Efinaconazole and H3 in Healthy Volunteers

| Parameter | Efinaconazole (mean +/− SD) [range] | | H3 metabolite (mean +/− SD) (range) | |
|---|---|---|---|---|
| | Day 1 | Day 10 | Day 1 | Day 10 |
| $C_{max}$ (ng/mL) | 0.38 ± 0.39 [0.12-1.11] | 0.54 ± 0.22 [0.25-0.85] | 0.44 ± 0.36 [0.15-1.31] | 1.63 ± 0.80 [0.46-2.62] |
| $T_{max}$ (h) | 24 [6-28] | 10 [0-24] | 48 [2-72] | 1 [0-28] |
| $C_{min}$ (ng/mL) | 0.05 [0-0.14] | 0.47 ± 0.18 [0.25-0.85] | 0.17 ± 0.23 [0-0.55] | 1.54 ± 0.77 [0.39-2.62] |
| $AUC_{24h}$ (ng * h/mL) | 2.64 ± 2.85 [0.47-7.31] | 9.48 ± 3.86 [4.89-15.78] | 5.65 ± 5.30 [0.41-12.4] | 32.5 ± 14.7 [10-50] |

On day 1, efinaconazole and H3 were detectable in plasma in at least one time point in most subjects; plasma concentration range was 0-1.11 and 0-1.31 ng/mL, respectively. On day 10, efinaconazole and H3 plasma concentration range was 0.25-0.85 and 0.39-2.62 ng/mL, respectively. The average efinaconazole and H3 plasma concentration was 0.37 and 1.27 ng/mL, respectively. Mean $C_{max}$ were 0.382 ng/mL and 0.436 ng/mL for efinaconazole and H3 on day 1, and 0.542 ng/mL and 1.628 ng/mL on day 10, respectively. Systemic efinaconazole and H3 exposure ($AUC_{24h}$) was approximately 3.6-fold and 5.8-fold greater on day 10 than on day 1, respectively. Thus, efinaconazole accumulated after repeat application. There were no meaningful differences in trough plasma levels (at 24 hours post dose) between days 8, 10, and 11, suggesting that steady-state was reached for efinaconazole and H3 by day 8 (5th application).

Of the 19 onychomycosis patients who completed the PK study, one was excluded from the PK analyses due to presumed contamination of pre-dose blood/plasma samples. The plasma concentration-time profiles for efinaconazole and H3 showed that the mean concentrations generally plateaued with no marked spikes over the course of each PK day. Efinaconazole concentrations were generally higher than those of H3 on day 1. However, H3 mean concentrations were markedly greater than those of efinaconazole on days 14 and 28. Both efinaconazole and H3 mean $C_{max}$ increased slightly at each assessment period, reaching 0.67 and 2.36 ng/mL, respectively, on day 28. The mean $AUC_{24h}$ for efinaconazole increased from 1.79 ng*h/mL on day 1, to 12.15 ng*h/mL on day 28, indicating accumulation after multiple doses. The mean $AUC_{24h}$ for H3 systemic exposure, as measured by $C_{max}$ and $AUC_{24h}$, was comparable between days 14 and 28 (Table 5); further, trough and 24 h plasma levels were similar on both days. Thus, steady state appeared to be reached by day 14 of dosing. Two weeks after the last dose, efinaconazole and H3 were detected in plasma from several subjects at mean concentrations of 0.07 and 0.31 ng/mL, respectively, suggesting a long apparent elimination half-life ($t_{1/2}$).

TABLE 5

Pharmacokinetic Parameters of Efinaconazole and H3 in Onychomycosis Patients.

| Parameter | Efinaconazole (mean +/− SD) [range] | | | H3 metabolite (mean +/− SD) [range] | | |
|---|---|---|---|---|---|---|
| | Day 1 | Day 14 | Day 28 | Day 1 | Day 14 | Day 28 |
| $C_{max}$ (ng/mL) | 0.23 ± 0.18 [0.0-0.67] | 0.62 ± 0.23 [0.14-0.99] | 0.67 ± 0.37 [0.18-1.47] | 0.09 ± 0.14 [0.00-0.44] | 2.20 ± 1.72 [0.58-7.45] | 2.36 ± 1.64 [0.53-5.55] |
| $C_{min}$ (ng/mL) | Not calculated | 0.33 ± 0.17 [0.01-0.63] | 0.36 ± 0.20 [0.11-0.72] | Not calculated | 1.47 ± 1.27 [0.20-5.07] | 1.67 ± 1.17 [0.29-4.07] |
| $T_{max}$ (h) | 23.92 [6.03-24.00] | 4.55 [0.0-24.00] | 16 [0.0-24.00] | 23.92 [23.92-24.00] | 1.00 [0.0-16.00] | 0.00 [0.0-24.00] |
| $AUC_{24\,h}$ (ng*h/mL) | 1.79 ± 2.04 [0.30-7.05] | 10.9 ± 5.90 [0.39-19.54] | 12.15 ± 6.91 [1.46-25.25] | 1.50 ± 1.13 [0.60-3.61] | 40.03 ± 34.02 [7.42-141.49] | 45.80 ± 31.85 [8.53-113.40] |

A majority of the subjects within each active treatment group had undetectable or low plasma concentrations of IDP-108 (0.000-7.050 ng/mL) and its H3 metabolite (0.000-5.680 ng/mL) beginning at Week 4 and continuing until the end of the treatment period at Week 36. A majority of the subjects who had measurable IDP-108 and H3 metabolite concentration levels during the treatment period had levels that were below the limit of quantification by the 30-day post-treatment follow-up visit. The systemic exposure to IDP-108 and its H3 metabolite was low and there were no substantive differences in this respect between subjects in the active treatment groups. Overall, the plasma concentrations of IDP-108 and of the H3 metabolite of IDP-108 across the active treatment groups were less than or equal to 7.050 ng/mL and 5.680 ng/mL, respectively, at all time points.

The H3 metabolite is the only major plasma metabolite. While the plasma concentration of the H3 metabolite was generally greater than the plasma concentration of efinaconazole, the concentration was low and no substantial accumulation was observed following long term exposure (up to 36 weeks of once daily treatment with IDP-108).

The 2006 Food and Drug Administration Drug Interaction Studies—Study Design, Data Analysis, and Implications for Dosing and Labeling draft guidance recommends clinical evaluation for drugs that are CYP inhibitors if the mean steady state $C_{max}/K_i$ is greater than 0.1. Based on in vitro efinaconazole CYP inhibition data for the most sensitive isoform, i.e., CYP2C9 with $K_i$ of 91 ng/mL, the steady state $C_{max}/K_i$ is 0.007, significantly below this threshold value. Given the relatively low exposure levels, and the steady state $C_{max}/K_i$ ratio based on in vitro efinaconazole cytochrome P (CYP) inhibition data for the most sensitive isoform (CYP2C9; mean $C_{max}$=0.67 ng/mL, $K_i$=91 ng/mL, $C_{max}/K_i$=0.007), there are no safety concerns associated with the potential for drug-drug interactions.

Plasma levels of both efinaconazole and its H3 metabolite were negligible after single and repeat applications of IDP-108 to toenails. Plasma levels of the H3 metabolite were consistently higher than that of efinaconazole. The absorption of IDP-108 did not appear to differ considerably between topical applications to the toenail and topical applications to back skin. Further, the study results indicated that the systemic bioavailability of efinaconazole was relatively the same following one and seven applications of IDP-108 to the skin on the back of healthy volunteers.

In one study it was noted that, after a single topical application steady-state was reached for efinaconazole on Day 8 (equating to the fifth topical application) for both toenails and back skin.

IDP-108 had low systemic exposures of efinaconazole and its H3 and H4 metabolites when applied once daily for 28 days to all 10 toenails. By the end of the treatment period, the mean concentrations of the H3 metabolite were greater than the mean concentrations of IDP-108; the maximum mean H3 metabolite concentration, however, was low and less than 2.4 ng/mL on Day 28 along with a barely detectable IDP-108 concentration at the final assessment period. The H4 metabolite showed no meaningful systemic availability, with a mean maximum concentration of approximately zero during the final assessment period.

The following articles are incorporated by reference herein as providing additional data, methods, compositions, techniques, and concepts that relate to the inventive methods described herein: Jarratt et al., Journal of Drugs in Dermatology, 12(9):1010 (September 2013); Tschen et al., Journal of Drugs in Dermatology, 12(2):186 (February 2013); Del Rosso et al., Journal of Clinical and Aesthetic Dermatology, 6(3): 20 (March 2013); Bikowski, J., Practical Dermatology, 37 (May 2013); Rich, P., CUTIS, 91:305 (June 2013); Pollak, R., Podiatry Today, 26(2) (February 2013); Siu et al., Antimicrob. Agents Chemother., 57(4):1610 (April 2013); Tatsumi et al., Antimicrob. Agents Chemother., 57(5):2405 (May 2013); Elewski et al., Journal of Drugs in Dermatology, 12(7)(suppl.):s96 (July 2013); Notabartolo, Journal of Dermatology for Physician Assistants, 7(3):13 (Summer 2013); and Tosti A., CUTIS, 92:203-208 (October 2013).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following aspects) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claim element as essential to the practice of the invention.

Any combination of the above-described elements in all possible variations thereof is encompassed by the invention unless otherwise indicated herein or otherwise clearly contradicted by context.

What is claimed is:

1. A method of treating onychomycosis comprising applying a pharmaceutically acceptable formulation once a day for a treatment period of at least 36 weeks to the treatment area of an onychomycosis patient (a) without debriding the nail or nail-associated tissue initially or during the treatment period and/or (b) without removing the formulation from the treatment area during the treatment period,
    wherein the formulation comprises 10% w/w efinaconazole, alcohol, cyclomethicone, diisopropyl adipate, either or both of C12-15 alkyl lactate and isopropyl myristate, an antioxidant, butylated hydroxytoluene (BHT), and a salt of disodium edetate ethylenediaminetetraacetic acid (EDTA).

2. The method of claim 1, wherein the method is performed (a) without debriding the nail or nail-associated tissue initially or during the treatment period and (b) without removing the formulation from the treatment area during the treatment period.

3. The method of claim 1, wherein the method is performed without occluding or partially occluding the nail or nail-associated tissue.

4. The method of claim 1, wherein the patient waits at least 10 minutes before administering the formulation if the treatment area was previously in contact with water.

5. The method of claim 1, wherein the method includes a step of cleaning the treatment area prior to administering the efinaconazole formulation.

6. The method of claim 1, wherein the patient cleans the treatment area prior to treatment and waits for at least 10 minutes before administering the formulation if the cleaning includes wetting the treatment area with water.

7. The method of claim 1, wherein the efinaconazole is the only active pharmaceutical ingredient in the formulation.

8. The method of claim 1, wherein the amounts of BHT and EDTA are sufficient to ensure the formulation is (i) colorless upon initial formulation and (ii) colorless or pale yellow after storage for at least three weeks at a temperature of about 40° C.

9. The method of claim 1, wherein the formulation further comprises water.

10. The method of claim 1, wherein the formulation further comprises citric acid.

11. The method of claim 1, wherein the treatment period is 48 weeks.

12. The method of claim 1, wherein the method comprises cutting nails once every two weeks or more frequently.

13. The method of claim 1, wherein the method does not comprise cutting nails more often than every two weeks.

14. The method of claim 1, wherein the efinaconazole formulation is not administered in an occluded or semi-occluded manner.

15. The method of claim 1, wherein the method comprises uniformly spreading the efinaconazole formulation throughout the treatment area with an applicator.

16. The method of claim 1, wherein the average amount of efinaconazole delivered to each $cm^2$ of the treatment area is about 0.15 $mg/cm^2$ to about 0.45 $mg/cm^2$.

17. The method of claim 1, wherein the method comprises administering the efinaconazole formulation from a container that is in fluid communication with an applicator, loading the applicator, and applying the efinaconazole with the applicator.

18. The method of claim 1, wherein performance of the method in a patient population results in a mycological cure rate of at least about 40%, a clinical efficacy rate of at least about 20%, a complete cure rate of at least about 10%, or a combination of any or all thereof.

* * * * *